United States Patent
Egli

(10) Patent No.: US 10,513,709 B2
(45) Date of Patent: *Dec. 24, 2019

(54) SOMATIC CELL NUCLEAR TRANSFER METHODS

(71) Applicant: New York Stem Cell Foundation, Inc., New York, NY (US)

(72) Inventor: Dietrich M. Egli, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,976

(22) Filed: Feb. 13, 2018

(65) Prior Publication Data

US 2018/0237799 A1 Aug. 23, 2018

Related U.S. Application Data

(63) Continuation of application No. 14/775,594, filed as application No. PCT/US2014/029295 on Mar. 14, 2014, now Pat. No. 9,896,699.

(60) Provisional application No. 61/947,353, filed on Mar. 3, 2014, provisional application No. 61/891,322, filed on Oct. 15, 2013, provisional application No. 61/793,492, filed on Mar. 15, 2013.

(51) Int. Cl.
| | |
|---|---|
| *C12N 15/00* | (2006.01) |
| *C12N 15/877* | (2010.01) |
| *C12N 5/0735* | (2010.01) |
| *C12N 5/075* | (2010.01) |

(52) U.S. Cl.
CPC ....... *C12N 15/8776* (2013.01); *C12N 5/0606* (2013.01); *C12N 5/0609* (2013.01); *C12N 2501/065* (2013.01); *C12N 2501/31* (2013.01); *C12N 2501/727* (2013.01); *C12N 2501/999* (2013.01); *C12N 2517/04* (2013.01); *C12N 2517/10* (2013.01); *C12N 2760/18845* (2013.01)

(58) Field of Classification Search
CPC .................................................. C12N 15/8776
USPC ........................................... 435/455; 800/24
See application file for complete search history.

(56) References Cited

U.S. PATENT DOCUMENTS

| | | | |
|---|---|---|---|
| 8,748,178 B2 | 6/2014 | Egli et al. | |
| 8,883,498 B2 | 11/2014 | Heike et al. | |
| 2002/0090722 A1 | 7/2002 | Dominko et al. | |
| 2012/0129260 A1 | 5/2012 | Egli et al. | |
| 2013/0040387 A1 | 2/2013 | Heike et al. | |
| 2014/0234968 A1* | 8/2014 | Chung | C12N 5/0606 435/449 |

FOREIGN PATENT DOCUMENTS

| | | |
|---|---|---|
| WO | WO 2008/103462 A2 | 8/2008 |
| WO | WO 2012/071393 A2 | 5/2012 |
| WO | WO 2014/186394 A1 | 11/2014 |

OTHER PUBLICATIONS

McElroy (Theriogenology, 2008, 69:416-425).*
Okada (Theriogenology, 2008, 69:416-425).*
Chung, Young Gie et al.: "Human Somatic Cell Nuclear Transfer Using Adult Cells", Cell Stem Cell, 14, Apr. 1, 2014, pp. 1-4.
Extended European Search Report dated Aug. 10, 2016, regarding EP 14763568.4.
French, Andrew J. et al.: "Development of Human Cloned Blastocysts Following Somatic Cell Nuclear Transfer with Adult Fibroblasts", Stem Cells., vol. 26, No. 2, Feb. 1, 2008, pp. 485-493.
McElroy, S.L. et al.: "Effects of culture conditions and nuclear transfer protocols on blastocyst formation and Mrna expression in pre-implantation procine embryos" Theriogenology, 2008, 69:416-425).
Noggle et al.: "Human Oocytes Reprogram Somatic Cells to a Pluripotent State," Nature (2011), 478:70-76, Macmillan Publishers Limited.
Okada, Yoshio et al.: "Sendai Virus-Induced Cell Fusion"; Methods of Enzymology, 1993, vol. 221, pp. 18-41.
Strelchenko, N. et al.: "Morula-derived human embryonic stem cells", Reproductive Biomedicine Online, Reproductive Healthcare Ltd, GB, vol. 9, No. 6, Jan. 1, 2004 pp. 623-629.
Su et al.: "Oxamflatin Significantly Improves Nuclear Reprogramming, Blastocyst Quality, and In Vitro Development of Bovine SCNT Embryos,"; PLoS ONE (2011), 6(8):1-14.
Tachibana, Masahito et al.: "Human Embryonic Stem Cells Derived by Somatic Cell Nuclear Transfer"; Cell, 153, 2013, pp. 1-11.
Tachibana, Masahito et al.: "Mitochondrial gene replacement in primate offspring and embryonic stem cells", Nature, vol. 461, No. 7262, Aug. 26, 2009, pp. 367-372.
Yamada, Mitsutoshi et al.: "Human oocytes reprogram adult somatic nuclei of a type 1 diabetic to diploid pluripotent stem cells", Nature, Apr. 28, 2014, 16 pages.

* cited by examiner

*Primary Examiner* — Valarie E Bertoglio
(74) *Attorney, Agent, or Firm* — DLA Piper LLP (US)

(57) ABSTRACT

The present invention provides methods for making reconstructed diploid human oocytes comprising the diploid genome of a human somatic cell, and also methods for making human nuclear transfer embryos, human embryonic stem cells, and human differentiated cells therefrom. The present invention also provides reconstructed human oocytes, human nuclear transfer embryos, human embryonic stem cells, and differentiated cells made using such methods, as well as compositions and kits useful in performing such methods.

8 Claims, 12 Drawing Sheets

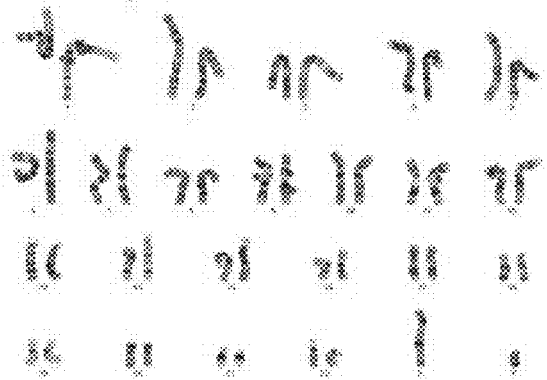
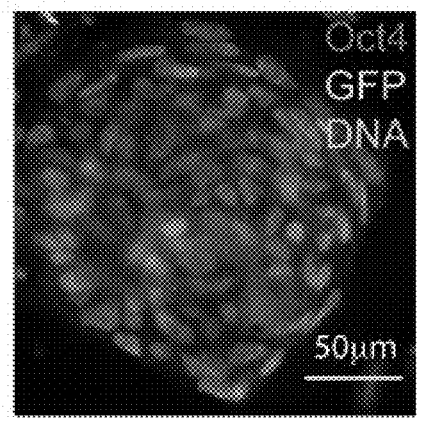
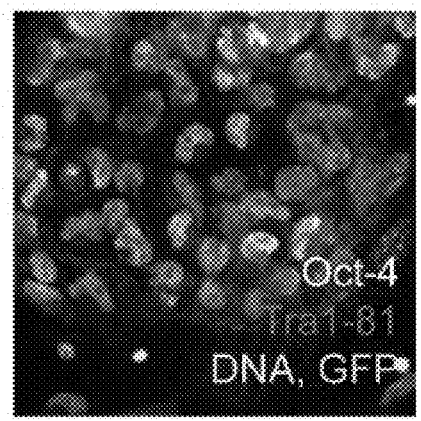
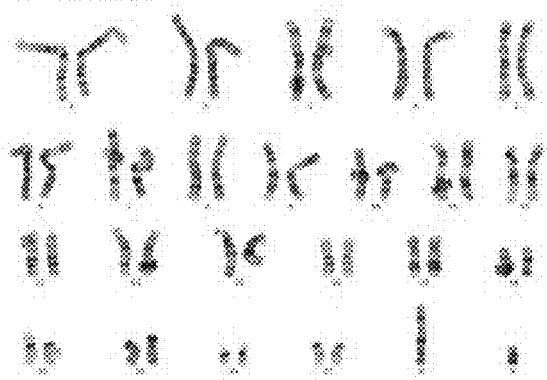
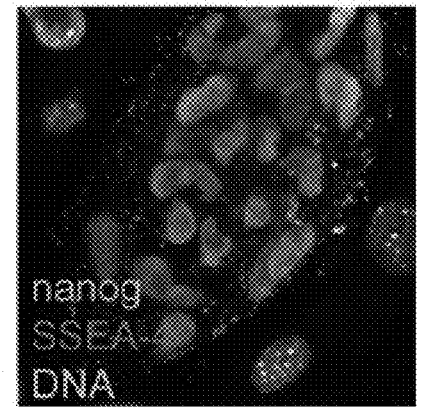
FIG. 8

FIG. 9A-I    FIG. 9K-9L

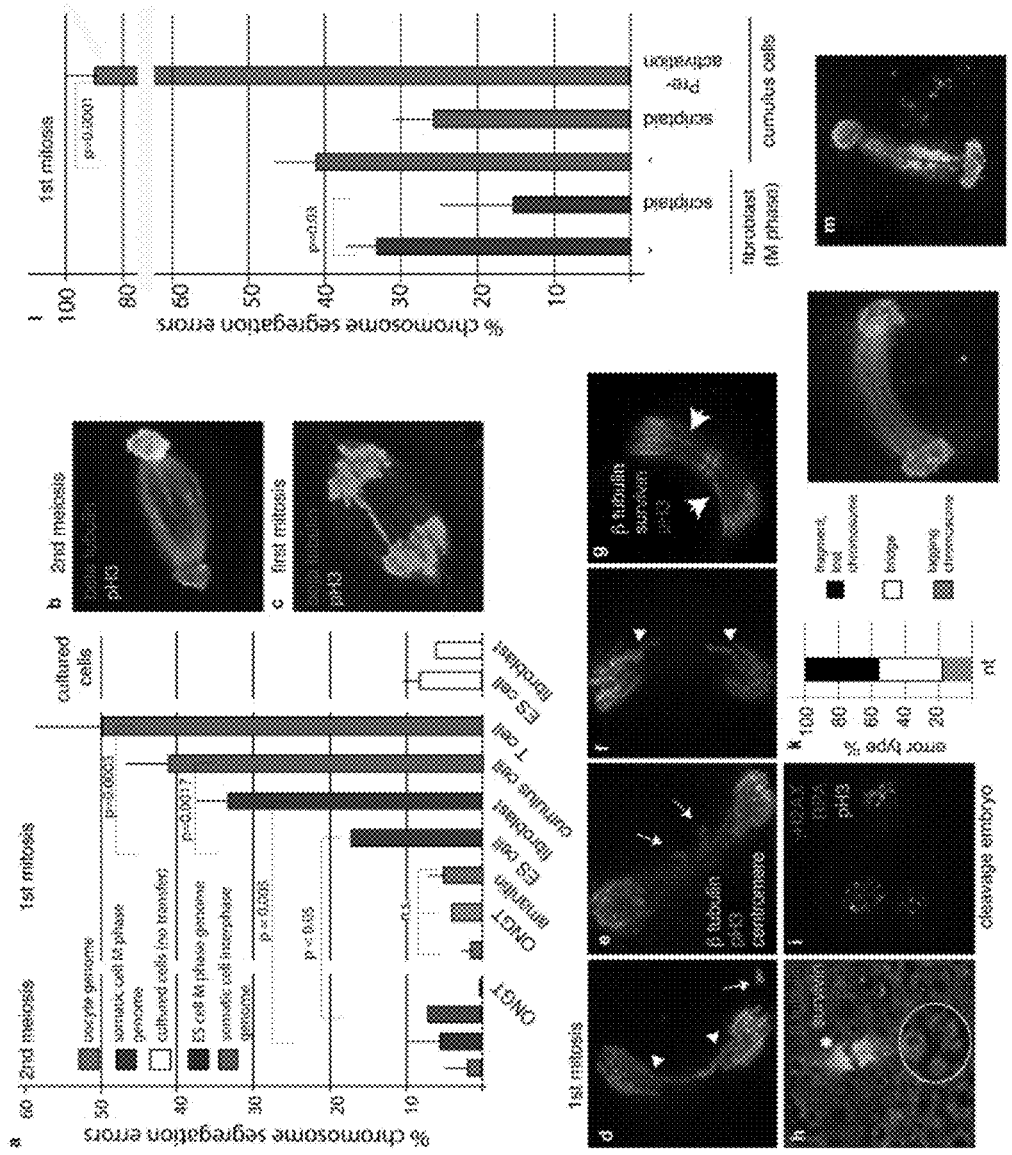
FIG. 13A-I  FIG. 13K-13M

SOMATIC CELL NUCLEAR TRANSFER METHODS

CROSS-REFERENCE TO RELATED APPLICATIONS

This application is a continuation application of U.S. application Ser. No. 14/775,594 filed Sep. 11, 2015, now issued as U.S. Pat. No. 9,896,699, which is a 35 USC § 371 National Stage application of International Application No. PCT/US2014/029295 filed Mar. 14, 2014; which claims the benefit under 35 USC § 119(e) to U.S. Application Ser. No. 61/947,353 filed Mar. 3, 2014, U.S. Application Ser. No. 61/891,322 filed Oct. 15, 2013 and to U.S. Application Ser. No. 61/793,492 filed Mar. 15, 2013. The disclosure of each of the prior applications is considered part of and is incorporated by reference in the disclosure of this application.

COPYRIGHT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

INCORPORATION BY REFERENCE

For countries and territories that permit incorporation by reference, the text of all documents cited herein is hereby incorporated by reference in its entirety.

BACKGROUND OF THE INVENTION

The cloning of frogs from somatic cells demonstrated that differentiation from the zygote into specialized cell types was a reversible process. The transplantation of somatic nuclei into unfertilized mammalian oocytes resulted in the cloning of sheep, mice, cows and various other mammalian species.

The derivation of embryonic stem cells from human blastocysts brought the prospect of combining nuclear transfer and stem cell derivation to generate cells and tissues for patients requiring replacement of diseased cells or tissue. This concept was realized in the mouse for the correction of immunodeficiency and of Parkinson's disease (Rideout et al. 2002 Cell 109(1): 17-27). Nuclear transfer stem cells were also derived from the rhesus monkey (Byrne et al., 2007 Nature 450 (7169): 497-502). However, most previous attempts at human somatic cell nuclear transfer (SCNT) using human cells have resulted in the generation of nuclear transfer embryos that consistently arrest at the late cleavage stages with karyotypic and transcriptional defects, prohibiting further development or stem cell derivation. Prior to the present invention, the only SCNT methods that were shown to be effective in generating human blastocyst stage embryos and stem cells derived therefrom were those that involved transferring a diploid human somatic cell genome into a haploid human oocyte without removing the oocyte's genome. (See Noggle et al. 2011. Human oocytes reprogram somatic cells to a pluripotent state. Nature 478(7367): 70-75. See also, U.S. Patent Application Pub. No.: US 2012/0129620). Such methods resulted in the generation of embyros and stem cells that were triploid. Thus, prior to the present invention there remained a need in the art for a method of generating a diploid human nuclear transfer embryo capable of developing to the blastocyst stage and from which diploid human pluripotent stem cells could be derived.

SUMMARY OF THE INVENTION

The present invention provides methods by which a human diploid embryo can be generated by somatic cell nuclear transfer. In some embodiments such methods involve transferring the diploid genome from a human somatic cell into an enucleated human oocyte cell, resulting in reprogramming of the somatic cell genome to an embryonic state. Using such methods the resulting reconstructed oocytes are able to develop to into blastocyst stage embryos having an inner cell mass. Furthermore, the present invention provides methods by which such blastocyst stage embryos can be used to derive diploid pluripotent stem cells (embryonic stem cells) containing a somatic cell genome that has been reprogrammed to an embryonic state. The present invention also provides methods of obtaining differentiated cells from such pluripotent stem cells. These and other aspects of the present invention are further described throughout the specification, claims, and drawings of this patent application.

In some aspects the present invention provides several important improvements over and above prior methods that result in improved development. These improvements include, but are not limited to, the following. First, in some embodiments the methods of the present invention are designed to maintain plasma membrane integrity during oocyte preparation and during cell/nuclear fusion. Second, in some embodiments the methods of the present invention are designed to minimize the negative consequences of compromised plasma membrane integrity, should it occur, by using calcium-free media, calcium chelators, and phosphatase inhibitors, either alone or in combination. Third, in some embodiments the methods of the present invention are designed to enable rapid and efficient activation of human oocytes using, for example using dual inhibition of both translation and meiotic kinase activity. Fourth, in some embodiments the methods of the present invention are designed to maximize reprogramming by improving replication and segregation of the somatic cell genome in the activated egg. Chromosome mis-segregation is frequent after somatic cell nuclear transfer. However, it is a discovery of the present invention that agents applied during the first cell cycle, such as histone deacetylase inhibitors and histone methylation inhibitors, can increase fidelity of chromosome duplication and enable efficient development to the blastocyst stage. These and other aspects of the present invention are described further below and thoughout the specification and claims of the present application.

It should be noted that while the methods of the present invention were created for, and shown to be effective in, human somatic cell nuclear transfer applications, the methods described herein may also be useful in other applications, including for nuclear transfer using non-human somatic cells and for nuclear transfer using non-somatic cells (such as oocyte nuclear transfer protocols). One of skill in the art will be able to appreciate those aspects of the invention described herein that can be applied equally to non-human somatic cell nuclear transfer methods and to non-somatic cell nuclear transfer methods. Thus, in some embodiments of the invention the methods described herein can be applied to non-human cells and to non-somatic cells. It should also be noted that the different aspects of the methods described herein can be performd in various different combinations and also that, in some embodiments, only particular aspects of the methods described herein need be performed. One of skill in the art will appreciate those aspects of the present methods that can be practiced alone, or in combination with other methods, and all such methods are intended to fall within the scope of this invention. For example, in embodiments of the invention that comprise multiple separate method steps, the individual method steps can also be used in isolation, or in conjunction with other methods. As described above, and throughout this specification, the methods of the present invention provide several improvements over and above prior methods. In some embodiments all of the improvements described herein are used, while in other embodiments only one such improvement (e.g., the use of a calcium-free medium and/or calcium chelator during nuclear transfer, the use of a low amount of fusogenic agent, the use of a translation inhibitor, the use of a meiotic kinase inhibitor, the use of a histone deacetylase inhibitor, etc.) need be used, and in yet other embodiments any combination of two or more of such improvements may be used, as desired.

In one embodiment the present invention provides a method for producing a diploid human nuclear transfer embryo capable of developing into a blastocyst containing an inner cell mass and/or from which embryonic stem (ES) cells can be derived, the method comprising: obtaining a diploid nuclear genome from a postnatal human somatic cell, such as an adult human somatic cell.

In one embodiment the present invention provides a method for producing a diploid human nuclear transfer embryo capable of developing into a blastocyst containing an inner cell mass and/or from which ES cells can be derived, wherein the method comprises transferring a diploid human somatic cell nuclear genome into an enucleated mature human oocyte in a medium that is calcium-free, and/or contains a calcium chelator, and/or contains a phosphatase inhibitor.

In one embodiment the present invention provides a method for producing a diploid human nuclear transfer embryo capable of developing into a blastocyst containing an inner cell mass and/or from which ES cells can be derived, wherein the method comprises transferring a diploid human somatic cell nuclear genome into an enucleated mature human oocyte using a fusogenic agent, wherein the concentration of the fusogenic agent is selected so as to minimize cell membrane damage while still being sufficient to induce cell fusion.

In one embodiment the present invention provides a method for producing a diploid human nuclear transfer embryo capable of developing into a blastocyst containing an inner cell mass and/or from which ES cells can be derived, wherein the method comprises transferring a diploid human somatic cell nuclear genome into an enucleated mature human oocyte using a fusogenic agent, wherein the fusogenic agent is contacted with a restricted area of the somatic cell and/or the oocyte so as to minimize cell membrane damage while still inducing cell fusion.

In one embodiment the present invention provides a method for producing a diploid human nuclear transfer embryo capable of developing into a blastocyst containing an inner cell mass and/or from which ES cells can be derived, the method comprising transferring a diploid human somatic cell nuclear genome into an enucleated mature human oocyte to form a reconstructed oocyte and subsequently activating the reconstructed oocyte by contacting it with one or more of a calcium ionophore, an inhibitor of translation, and an inhibitor meiotic kinases.

In one embodiment the present invention provides a method for producing a diploid human nuclear transfer embryo capable of developing into a blastocyst containing an inner cell mass and/or from which ES cells can be derived, the method comprising transferring a diploid human somatic cell nuclear genome into an enucleated mature human oocyte to form a reconstructed oocyte and subsequently activating the reconstructed oocyte by contacting it with a calcium ionophore and an inhibitor of translation.

In one embodiment the present invention provides a method for producing a diploid human nuclear transfer embryo capable of developing into a blastocyst containing an inner cell mass and/or from which embryonic stem ES cells can be derived, the method comprising transferring a diploid human somatic cell nuclear genome into an enucleated mature human oocyte to form a reconstructed oocyte and subsequently activating the reconstructed oocyte by contacting it with a calcium ionophore, an inhibitor of translation and an inhibitor meiotic kinases.

In one embodiment the present invention provides a method for producing a diploid human nuclear transfer embryo capable of developing into a blastocyst containing an inner cell mass and/or from which ES cells can be derived, the method comprising transferring a diploid human somatic cell nuclear genome into an enucleated mature human oocyte to form a reconstructed oocyte, activating the reconstructed oocyte, and contacting the reconstructed oocyte and/or embryo derived therefrom with a histone deacetylase inhibitor. In some such embodiments the reconstructed oocyte is contacted with the histone deacetylase inhibitor during its first cell cycle.

In one embodiment the present invention provides a method for producing a diploid human nuclear transfer embryo capable of developing into a blastocyst containing an inner cell mass and/or from which embryonic stem ES cells can be derived, the method comprising transferring a diploid human somatic cell nuclear genome into an enucleated mature human oocyte to form a reconstructed oocyte, activating the reconstructed oocyte, and contacting the reconstructed oocyte and/or embryo derived therefrom with a histone methylation inhibitor. In some such embodiments the reconstructed oocyte is contacted with the histone methylation inhibitor during its first cell cycle.

In one embodiment the present invention provides a method for producing a diploid human nuclear transfer embryo capable of developing into a blastocyst containing an inner cell mass, the method comprising: (a) obtaining a diploid nuclear genome from a postnatal human somatic cell, (b) obtaining an enucleated mature human oocyte, (c) transferring the diploid nuclear genome into the enucleated mature human oocyte to form a reconstructed oocyte, wherein the transferring is performed in a medium that is calcium-free, and/or contains a calcium chelator, and/or contains a phosphatase inhbitor, (d) subsequently contacting the reconstructed oocyte with a calcium ionophore, an inhibitor of translation, and an inhibitor meiotic kinases, to activate the reconstructed oocyte and promote entry into interphase, and (e) subsequently contacting the reconstructed oocyte with a histone deacetylase inhibitor and/or a histone methylation inhibitor, thereby producing a diploid human nuclear transfer embryo capable of developing into a blastocyst containing an inner cell mass.

In another embodiment the present invention provides a method for producing a diploid human nuclear transfer embryo capable of developing into a blastocyst containing an inner cell mass, the method comprising: (a) obtaining a diploid human somatic cell nuclear genome, (b) obtaining an enucleated mature human oocyte, (c) transferring the diploid human somatic cell nuclear genome into the enucleated mature human oocyte and/or fusing the diploid human somatic cell nuclear genome with the enucleated mature human oocyte to form a reconstructed oocyte, (d) activating the reconstructed oocyte using a calcium ionophore and one or more agents that rapidly inactivate meiotic kinases and promote entry into interphase, and (e) contacting the reconstructed oocyte with a histone deacetylase inhibitor, thereby producing a diploid human nuclear transfer embryo.

In another embodiment the present invention provides a method for producing a diploid human nuclear transfer embryo capable of developing into a blastocyst containing an inner cell mass, the method comprising: (a) obtaining a diploid human somatic cell nuclear genome, (b) obtaining an enucleated mature human oocyte, (c) fusing the diploid human somatic cell nuclear genome with the enucleated mature human oocyte using a fusogenic agent, to form a reconstructed oocyte, (d) subsequent to step c, activating the reconstructed oocyte using ionomycin, (e) subsequent to step d., contacting the reconstructed oocyte with one or more agents that rapidly inactivate meiotic kinases and promote entry into interphase, and one or more histone deacetylase (HDAC) inhibitors for approximately 4 to 4.5 hours, and (f) subsequent to step e., culturing the reconstructed oocyte in the presence of the HDAC inhibitors for an additional approximately 10-16 hours, thereby producing a diploid human nuclear transfer embryo.

In yet another embodiment, the present invention provides a method for producing a diploid human nuclear transfer embryo capable of developing into a blastocyst containing an inner cell mass, the method comprising: (a) obtaining a diploid human somatic cell nuclear genome, (b) obtaining an enucleated mature human oocyte, (c) fusing the diploid human somatic cell nuclear genome with the enucleated mature human oocyte using inactivated Sendai virus at around the lowest concentration at which fusion still occurs, (d) approximately 1-3 hours following step c, activating the reconstructed oocyte using approximately 3 µM ionomycin for approximately 5 minutes at approximately 37 degrees Celsius, (e) subsequent to step d., contacting the reconstructed oocyte with approximately 10 µM puromycin, approximately 2 mM 6-DMAP, and the histone deacetylase (HDAC) inhibitors Scriptaid and Nch51 for approximately 4 to 4.5 hours, and (f) subsequent to step e., culturing the reconstructed oocyte in the present of the HDAC inhibitors for an additional approximately 10-16 hours, thereby producing a diploid human nuclear transfer embryo.

In another embodiment the present invention provides a method for producing a diploid human nuclear transfer embryo capable of developing into a blastocyst, the method comprising: (a) obtaining a diploid human somatic cell nuclear genome, (b) obtaining an enucleated mature human oocyte, (c) transferring the diploid human somatic cell nuclear genome into the enucleated mature human oocyte to form a reconstructed oocyte, (d) activating the reconstructed oocyte, and (e) contacting the reconstructed oocyte with a histone deacetylase inhibitor.

In another embodiment, the present invention provides a method for producing a diploid human pluripotent stem cell from a diploid human somatic cell, the method comprising: (a) obtaining a diploid human somatic cell nuclear genome from a diploid human somatic cell, (b) obtaining an enucleated mature human oocyte, (c) transferring the diploid human somatic cell nuclear genome into the enucleated mature human oocyte to form a reconstructed oocyte, (d) activating the reconstructed oocyte using a calcium ionophore and one or more agents that rapidly inactivate meiotic kinases and promote entry into interphase, (e) contacting the reconstructed oocyte with a histone deacetylase inhibitor, thereby producing a diploid human nuclear transfer embryo, (f) culturing the diploid human nuclear transfer embryo in a medium that comprises FBS until it develops to into a blastocyst, (g) obtaining cells from the inner cell mass of the blastocyst, and (h) culturing the cells from the inner cell mass of the blastocyst to form a population of a diploid human pluripotent stem cells.

In another embodiment the present invention provides a method for producing a diploid human pluripotent stem cell from a diploid human somatic cell, the method comprising: (a) obtaining a diploid human somatic cell nuclear genome from a diploid human somatic cell, (b) obtaining an enucleated mature human oocyte, (c) fusing the diploid human somatic cell nuclear genome with the enucleated mature human oocyte using inactivated Sendai virus at around the lowest concentration at which fusion still occurs, to form a reconstructed oocyte, (d) approximately 1-3 hours following step c, activating the reconstructed oocyte using approximately 3 µM ionomycin for approximately 5 minutes at approximately 37 degrees Celsius, (e) contacting the reconstructed oocyte with approximately 10 µM puromycin, 2 mM 6-DMAP, and the histone deacetylase (HDAC) inhibitors Scriptaid and Nch51 for approximately 4 to 4.5 hours, (f) subsequently culturing the reconstructed oocyte in the present of the HDAC inhibitors for an additional approximately 10-16 hours, thereby producing a diploid human nuclear transfer embryo, (g) culturing the diploid human nuclear transfer embryo in a medium that comprises FBS until it develops to into a blastocyst, (h) obtaining cells from the inner cell mass of the blastocyst, and (i) culturing the cells from the inner cell mass of the blastocyst to form a population of a diploid human pluripotent stem cells.

In some embodiments the methods described herein may be modified such that the somatic cell nuclear genome is not transferred into an oocyte that has already been enucleated, but rather the somatic cell nuclear genome is transferred into a non-enucleated oocyte and the oocyte genome is then removed subsequently. For example, in one embodiment the present invention provides a method for producing a diploid human nuclear transfer embryo capable of developing into a blastocyst containing an inner cell mass, the method comprising: (a) obtaining a diploid human somatic cell nuclear genome, (b) obtaining a non-enucleated mature human oocyte, (c) transferring the diploid human somatic cell nuclear genome into the non-enucleated mature human oocyte and/or fusing the diploid human somatic cell nuclear genome with the enucleated mature human oocyte to form a triploid reconstructed oocyte, (d) subsequently removing the oocyte genome from the reconstructed oocyte, (e) subsequently activating the reconstructed oocyte using a calcium ionophore and one or more agents that rapidly inactivate meiotic kinases and promote entry into interphase, and (f) subsequently contacting the reconstructed oocyte with a histone deacetylase inhibitor, thereby producing a diploid human nuclear transfer embryo.

In some embodiments the present invention provides methods for generating pluripotent stem cells (e.g., ES cells) from blastocyst stage embryos generated using the methods described herein. Such stem cells can be generated from the inner cell mass of a blastocyst stage embryo made according to the methods of the invention. Methods for generating pluripotent stem cells (such as ES cells) from blastocyst stage embryos are known in the art and any suitable such methods can be used. For example, in one embodiment the inner cell mass of a blastocyst made using the methods of the invention is contacted with a human embryonic stem cell medium that comprises Rho kinase inhibitors, Y27632, and thiazovivin until an outgrowth of pluripotent stem cells is observed. In some embodiments this may take about 3 to about 14 days. In some embodiments this may take about 4 days. In another embodiment the trophectoderm of a blastocyst made using the methods of the invention is ablated, for example using a laser, and cells from the inner cell mass of the blastocyst are plated on a fibroblast feeder layer in human embryonic stem cell media supplemented with thiazovivin and Rock inhibitor. Any remaining non-inner cell mass cells may be ablated with a laser at this stage also. Such methods can result in an outgrowth of pluripotent stem cells from the plated inner cell mass, which can be expanded to form a population of pluripotent stem cells, which may be passaged and/or cryopreserved if desired.

In some embodiments the present invention provides human pluripotent stem cells (such as ES cells) made using the methods described herein. Such pluripotent stem cells (such as ES cells) are diploid and comprise a nuclear genome derived from a diploid human somatic cell.

In some embodiments the present invention also provides differentiated cells generated from such pluripotent stem cells, including, but not limited to, insulin producing cells, neurons, liver cells, heart cells, bone cells, gut cells, skin cells, hormone producing cells and blood cells.

In one embodiment the present invention provides a reconstructed human oocyte comprising a diploid nuclear genome obtained from a postnatal human somatic cell and cytoplasm from an enucleated mature human oocyte.

In one embodiment the present invention provides a diploid human nuclear transfer embryo comprising a diploid nuclear genome obtained from a postnatal human somatic cell, such as an adult human somatic cell.

In one embodiment the present invention provides a diploid human embryonic stem cell line comprising a diploid nuclear genome obtained from a postnatal human somatic cell, such as an adult human somatic cell.

In one embodiment the present invention provides a differentiated human cell derived from a human embryonic stem cell comprising a diploid nuclear genome obtained from a postnatal human somatic cell, such as an adult human somatic cell. In one such embodiment the present invention provides an insulin-secreting cell derived from a human embryonic stem cell comprising a diploid nuclear genome obtained from a postnatal human somatic cell, such as an adult human somatic cell. In one such embodiment the somatic cell is obtained from a postnatal human subject having diabetes, such as an adult human subject having type I diabetes. A kit for use in a nuclear transfer method comprising: a calcium-free nuclear transfer medium.

In some embodiments the present invention provides kits comprising compositions and reagents useful in performing nuclear transfer methods. Such kits, and the compositions and reagents they contain, were invented in the course of developing the improved human somatic cell nuclear transfer protocols described herein. However, such kits, and the compositions and reagents they contain, may also be useful in other nuclear transfer applications, such as in protocols for nuclear transfer using non-human cells and in protocols for nuclear transfer using non-somatic cells, such as oocyte nuclear transfer protocols.

In one such embodiment the present invention provides a kit for use in a nuclear transfer method, the kit comprising one or more of the following components: (a) a nuclear transfer medium (wherein the nuclear transfer medium is calcium free and/or comprises a calcium chelator, a protein phosphatase inhibitor, and/or a fusogenic agent), (b) an activation medium (wherein the activation medium comprises one or more of a calcium ionophore, a protein translation inhibitor, and a meiotic kinase inhibitor), (c) an embryo culture medium (wherein the embryo culture medium comprises one or more of a histone deacetylase inhibitor, a histone methylation inhibitor, a protein translation inhibitor, and a meiotic kinase inhibitor), and (d) an ES cell derivation medium (wherein the ES cell derivation medium comprises fetal bovine serum (FBS)). In some such embodiments two or more of the above components are used. In some such embodiments three or more of the above components are used. In some such embodiments four or more of the above components are used.

These and other embodiments of the present invention are described throughout the specification, claims, and drawings of the present patent application.

BRIEF DESCRIPTION OF THE DRAWINGS

FIG. 8 |Karyotypes and pluripotency marker expression in three NT-ES cell lines derived from male foreskin BJ fibroblasts. The somatic donor cell used for transfer carries a GFP transgene.

FIGS. 13A-13I, 13K-13M. Segregation errors can be reduced using epigenetic modifiers. All transfers were performed into enucleated mouse oocytes. a, percentage of nuclear transfer embryos with an error in chromosome segregation. Shown is the dependence of segregation error on the source of origin of the nuclear genome. Note that few errors occur after transfer of oocyte genomes, mitotic errors are slightly elevated after transfer of embryonic stem cell genomes, and are greatly increased upon transfer of somatic cell genomes. b, normal chromosome segregation after nuclear transfer of a mitotic fibroblast genome. c, chromosome bridge at the first mitosis. d-g, different types of segregation abnormalities, and the localization of the centromeres. h, chromatin trapped in the midbody in a 2-cell stage embryo. The interphase nucleus is circled. Note the persistent phosphorylation of histone H3 in the vicinity of the chromosome passenger complex component survivin. i, DNA damage in a cleavage stage embryo. k, frequency of a particular segregation error in affected embryos. l, segregation errors upon treatment with HDAC inhibitor and kinase inhibitor. Note that histone deacetylation inhibitor reduces the frequency of segregation errors. m, mitotic chromosome segregation upon transfer of somatic cells after oocyte activation.

DETAILED DESCRIPTION OF THE INVENTION

Figure 1:
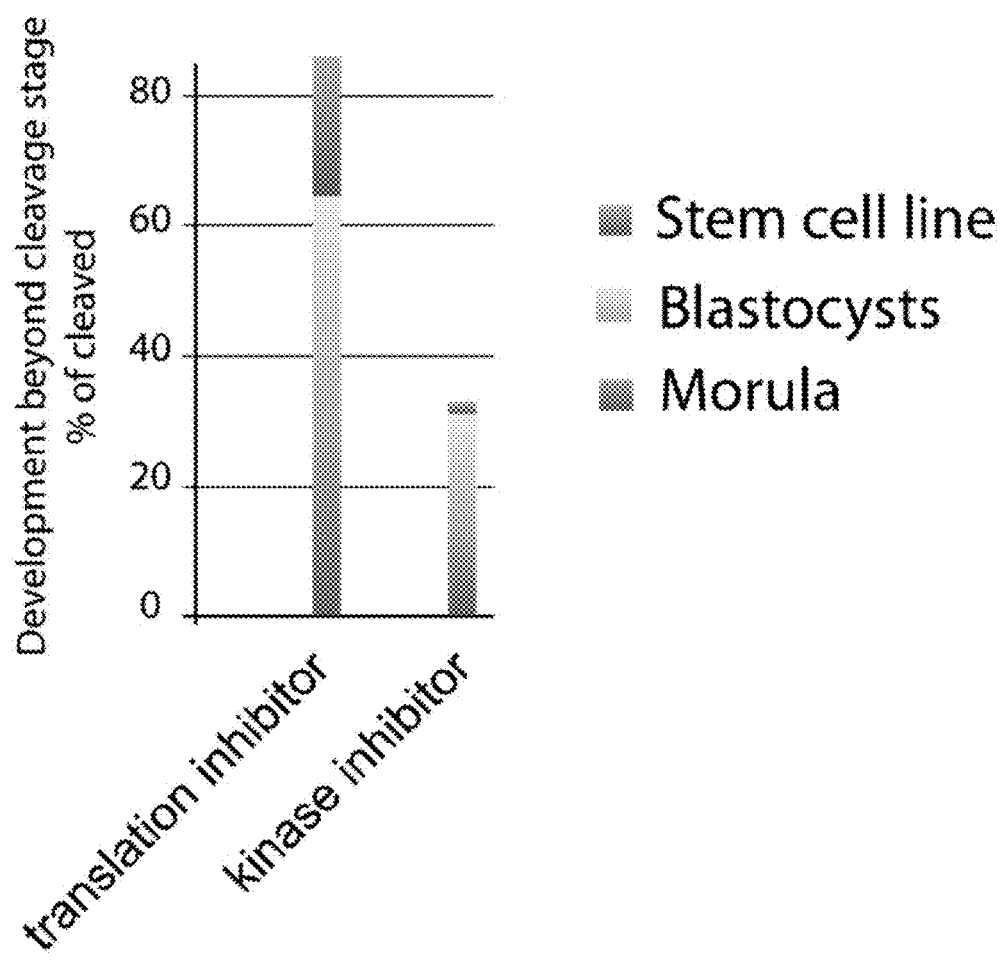
FIG. 1 |Efficiency of parthenogenetic development beyond the cleavage stage. Shown is the percentage of oocytes giving rise to stem cell lines, blastocysts but no stem cell lines, and morulas as the percentage of the number of oocytes cleaved. Data are from references 14 and 16 (see Reference List) and displayed here in a direct comparison.

A variety of techniques for somatic cell nuclear transfer and for the generation of somatic cell nuclear transfer embryos were previously known in the art, for example those that have been used for the cloning of animal species, including sheep (Wilmut et al., 1997 Nature 385, 810-813; WO 97 07669), mice (Wakayama et al., 1998 Nature 394, 369-374; WO 99 37143), cattle (Wells et al., 1999 Biol. Reprod. 60, 996-1005), goats (Baguisi et al., 1999 Nature Biotechnol. 17, 456-461; WO 00 25578), pigs (Polejaeva et al., 2000 Nature 407, 86-90) and rabbits (Chesne et al., 2002 Nature Biotechnol. 20, 366-369). Methods for nuclear transfer had also been described previously by Campbell et al. (Nuclear transfer in practice, School of Biosciences, University of Nottingham, Leicestershire, United Kingdom). However, to the best of the inventors' knowledge, prior to the present invention nobody had successfully produced a diploid human nuclear transfer embryo containing a diploid human genome from a postnatal or adult human somatic cell that was capable of developing into a blastocyst-stage embryo, and from which embryonic stem (ES) cells (or lines of ES cells) could be reliably obtained. The present invention provides various modifications and improvements to previously used nuclear transfer techniques that allow such human nuclear transfer embryos and ES cell lines to be reliably obtained—even when using adult somatic cells. For example, some of the modified and improved nuclear transfer methods described herein have been designed specifically to: (a) allow maintenance of plasma membrane integrity during oocyte preparation and during cell/nuclear fusion, (b) minimize the negative consequences of compromised plasma membrane integrity, should it occur, (c) enable rapid and efficient activation of oocytes after nuclear transfer, and (d) maximize reprogramming by improving replication and segregation of the somatic cell genome in the activated egg.

The major embodiments of the present invention are described in the above "Summary of the Invention" section of this application, as well as in the Detailed Description, Examples, Figures, and Claims sections of this patent application. All of such sections of this patent application are intended to be read together and in conjunction with one another, and the various embodiments described herein are intended to be combined in various ways, as will be apparent to those of skill in the art.

As used herein, the term "pluripotent stem cell" refers to a cell capable of differentiating into tissues of all three germ or dermal layers: mesoderm, endoderm, and ectoderm, unless otherwise specified.

As used herein the term "reconstructed oocyte" refers to an oocyte that has been enucleated (i.e., had its native nuclear genome removed) and into which a diploid somatic cell nuclear genome has been introduced.

As used herein, the term "embryo" refers to an activated oocyte that has divided to the two cell stage or beyond, e.g., to the four-cell, eight-cell, sixteen-cell or higher stages of embryonic development, unless otherwise specified.

As used herein, the phrase, "nuclear transfer embryo" refers to an embryo produced by inserting a nuclear genome derived from a somatic cell into an oocyte, or to an embryo produced from a "reconstructed oocyte" as defined above. The somatic cell will typically be obtained from a postnatal human, such as a human child or adult. A "nuclear transfer embryo" according to the invention is distinguished from a conventionally produced human embryo, such as that produced by the penetration of an ovum by a sperm.

Oocytes

As described elsewhere herein, the present invention provides various modifications and improvements to previously used somatic cell nuclear transfer techniques which allow human nuclear transfer embryos and human ES cell lines to be reliably obtained. Some of these improvements involve optimizing the preparation and handling of oocytes for use in the nuclear transfer methods of the invention, for example in order to maintain plasma membrane integrity of the oocyte, and/or in order to minimize calcium influx through a compromised oocyte plasma membrane integrity and/or minimize any negative consequences of such calcium influx. Some of the main ways in which this can be achieved are described below in the "nuclear transfer" section—which describes ways in which both oocytes and somatic cells can be handled in order to avoid compromising membrane integrity, minimize calcium influx, and minimize the negative consequences of any such calcium influx. In some embodiments, the present invention also provides other improved methods for handling oocytes that can result in improved oocyte and embryo development. For example, in embodiments where enzymes are used during oocyte preparation to remove cumulus cells (e.g., cumulase enzymes), exposure to such enzymes is minimized. For example, in one embodiment, after treatment with cumulase or some other suitable enzyme, the cumulus cells are mechanically removed and then the enzyme is removed.

Oocytes for use in the methods of the present invention can be obtained from any suitable source. For example oocytes may be obtained from human patients who have given their informed consent for the use of their oocytes in the methods described herein. Such patients may be, for example, undergoing fertility treatments, such as in vitro fertilization (IVF) treatments and/or other assisted reproduction techniques.

Exemplary methods for obtaining and manipulating human oocytes are well known in the art, and any such suitable method can be used. For example, in some embodiments human oocytes are obtained after controlled ovarian stimulation (COH), such as is routinely performed in in vitro fertilization clinics. For example, oocytes may be obtained following stimulation of ovulation with a hormone such as human chorionic gonadotropin ("hCG"). In some embodiments oocytes may be obtained from a human subject 30 to 40 hours after administration of an ovulation stimulus, such as hCG or leuprolide acetate, to the subject. In some embodiments the oocytes may be obtained from a human subject less than 36 hours after administration of an ovulation stimulus, or 35 hours after administration of an ovulation stimulus, or less than 35 hours after administration of an ovulation stimulus. One exemplary COH protocol consists of daily subcutaneous rFSH (recombinant follicle stimulating hormone) injections starting on day 2 of the menstrual cycle with the addition of a daily GnRH antagonist (such as Ganirelix) starting on day 6 of stimulation. Final oocyte maturation and ovulation may be triggered after reaching a follicle size of 18 mm by treatment with 4 mg of a GnRH agonist (such as Lupron) and 1000 IU of hCG (human chorionic gonadotropin). Using such methods, oocytes may be retrieved 35 hours post induction of ovulation.

In some embodiments of the present invention the oocytes used may have been cryopreserved prior to use (for example in the form of an intact oocyte or after enucleation). In alternative embodiments fresh (i.e., not previously cryopreserved) oocytes or enucleated oocytes may be used in the methods of the invention. When frozen oocytes are used any suitable freezing (cryopreservation) method known in the art may be used. For example, cryopreservation techniques are routinely used in fertility clinics to preserve and/or bank human oocytes for use in IVF procedures, and such methods can be used in conjunction with the present invention.

Methods for enucleating oocytes are well known in the art. Exemplary methods for enucleation of oocytes are provided in the Examples section of this patent application.

Somatic Cells

Somatic cells for use in the nuclear transfer methods described herein can be any suitable somatic cells. In some embodiments the somatic cells are from a postnatal human.

In some embodiments the somatic cells are from an adult human. Any suitable type of somatic cell can be used, including, but not limited to, fibroblasts and the like. In some embodiments of the present invention, the diploid human somatic cell, or the genome therefrom, is at the G0 or G1 stage of its cell cycle. Somatic cells in the G0 stage may be obtained by growing the cell to confluence in vitro (typically less than 0.5% of the cells will be in S-phase after growth to confluence). In other embodiments the diploid human somatic cell, or the genome therefrom, is at the M (or mitosis) stage of its cell cycle. As described below in the oocyte activation section, when M-phase somatic cells (or nuclear genomes) are used, oocytes may be activated with medium containing a translation inhibitor (such as puromycin) for a suitable time (such as 4 hours), without the need to also use a meiotic kinase inhibitor (such as 6-DMAP). In some embodiments the entire somatic cell, including the nuclear genome and the somatic cytoplasm, is transferred into the enucleated oocyte. The somatic cell nuclear genome comprises the nuclear DNA of a somatic cell, for example in the form of chromosomes, and may be within an intact somatic cells, a nucleus, or a "karyoplast" that comprises the nuclear DNA and a small amount of cytoplasm surrounded by a membrane, such as nuclear membrane and/or cell membrane.

Methods for obtaining and culturing somatic cells are well known in the art. Exemplary methods for obtaining and culturing somatic cells are provided in the Examples section of this patent application.

Nuclear Transfer

In some embodiments the methods of the present invention involve the transfer of a diploid nuclear genome from a somatic cell into an enucleated oocyte. The diploid nuclear genome can be transferred in a variety of different forms. For example, and as illustrated in the Examples section of this patent application, the diploid nuclear genome can be located within the somatic cell when it is transferred—such the entire somatic cell is introduced into, or fused with, the enucleated oocyte. However, in some embodiments the diploid nuclear genome may first be removed from the somatic cell prior to transfer. In such embodiments the nuclear genome may comprise only the nuclear DNA (for example in the form of chromosomes, such as metaphase chromosomes), or may be within a nucleus, or may be within a "karyoplast" that comprises the nuclear DNA and a small amount of cytoplasm surrounded by a membrane. Regardless of whether the somatic cell nuclear genome used in the methods of the present invention is present in a whole somatic cell, in a cell nucleus, in a karyoplast, or in some other form, the methods described herein may be referred to interchangeably as "nuclear transfer" methods or "cell fusion methods" and these terms are not intended to be limiting in any way.

As described elsewhere herein, an important aspect of the nuclear transfer methods of the present invention is that the protocols have been optimized to minimize membrane damage and to maintain the integrity of the meiotic arrest during the nuclear transfer process. As demonstrated in the Examples section of this patent application, compromised membrane integrity can result in unwanted calcium influx, which can in turn, compromise the meiotic state. Such membrane damage and calcium influx can be caused, for example, by the agents and methods used to promote nuclear transfer/cell fusion.

In some of the embodiments described herein, the step of transferring and/or fusing a diploid human somatic cell, or nuclear genome therefrom (e.g., in a nucleus or in a karyoplast), into/with an enucleated mature human oocyte comprises using a fusogenic agent. The term "fusogenic agent" is used herein to refer collectively to fusion-promoting chemicals and other agents (such as inactivated viruses, portions of inactivated viruses, or proteins derived from viruses) that can be used to fuse a somatic cell (or nucleus, nuclear genome, or karyoplast from a somatic cell) with an oocyte. In embodiments where a fusogenic agent is used, any suitable fusogenic agent known in the art may be used. In one embodiment the fusogenic agent may be polyethylene glycol. In one embodiment the fusogenic agent may be a Sendai virus, such as an inactivated Sendai virus. In some embodiments inactivated Sendai virus HVJ-E may be used. As described above, it is a particular finding of the present invention that exposure to fusogenic agents can be controlled so as to minimize membrane damage and the associated unwanted influx of calcium during and after the nuclear transfer process. Thus, in some embodiments the fusogenic agent, such as inactivated Sendai virus, is used at a low concentration, and preferably at the minimum dosage, amount, or concentration that can be readily used while still allowing fusion to occur. Using the fusogenic agent, such as Sendai virus, at a low concentration helps to minimize exposure to the fusogenic agent and is desirable because fusogenic agents can compromise membrane integrity leading to undesirable calcium influx. Using a low concentration of the fusogenic agent, such as Sendai virus, minimizes this source of calcium influx into the oocyte during the nuclear transfer process. Thus in some embodiments the fusogenic agent used, and/or the amount of the fusogenic agent used, is selected so as to minimize or eliminate calcium influx into the oocyte during the nuclear transfer process. One of skill in the art can readily determine a suitable amount of a fusogenic agent to use by, for example, performing a dose/response study and looking at the effects of the fusogenic agent on calcium influx and/or fusion. In one embodiment of the invention, where inactivated Sendai virus is used as the fusogenic agent, Sendai virus HVE-J from Genome One Cosmobio is reconstituted according to the manufacturer's instructions and then diluted 1:10 to 1:20 in a suitable medium. The resulting concentration of the inactivated Sendai virus HVE-J is low but sufficient to induce fusion. Similarly, in some embodiments exposure to the fusogenic agent is minimized in other ways, for example by only exposing a small area of the somatic cell or oocyte to the fusogenic agent, for example only exposing one side of the cell or one portion of the cell to the fusogenic agent. In one such embodiment, exposure to the fusogenic agent may be minimized by first aspirating the somatic cell into the pipette to be used for nuclear transfer/cell fusion and then subsequently aspirating fusogenic agent (such as Sendai virus) into the pipette, such that the somatic cell will then only be exposed to the fusogenic agent on one side. The side of the somatic cell exposed to the fusogenic agent may then be juxtaposed with the plasma membrane of the oocyte to allow nuclear transfer/cell fusion. In this way, injection of fusogenic agent below the plasma membrane of the somatic cell and/or the oocyte is avoided.

In some embodiments of the present invention nuclear transfer/cell fusion may be achieved using an "electrofusion" method that comprises administering an electrical pulse. However, in other embodiments the present methods do not comprise using electrofusion or administering an electrical pulse during the nuclear transfer/cell fusion step.

Whichever method is used to perform the nuclear transfer/cell fusion step (e.g., whether a fusogenic agent is used, electro-fusion is performed, or some other method is used), the present invention provides methods and compositions that can be used during and after the nuclear transfer/cell fusion step to minimize the detrimental effects of calcium influx that can otherwise occur during these procedures. Thus, in some of the embodiments of the present invention the step of transferring and/or fusing a diploid human somatic cell genome into/with the enucleated mature human oocyte is performed in a calcium-free medium, which may be referred to as a calcium-free nuclear transfer medium or a calcium-free cell fusion medium. Such a calcium-free medium may be used during and after nuclear transfer/cell fusion, and may be used until the oocyte is activated, or up to about one hour or two hours prior to activation. For example, and as shown in the Examples herein, it has been found that use of a calcium-free medium during nuclear transfer results in significantly improved results, including improved developmental potential of the resulting reconstructed oocytes and nuclear transfer embryos, improved frequency of derivation of diploid stem cell lines (ES cell lines), and improved ability to derive ES cells lines from both postnatal and adult human somatic cells—which had not been achieved previously by others using other methods. Exemplary calcium-free nuclear transfer media are described in the Examples herein. In addition, one of skill in the art can readily prepare calcium-free media using principles known in the art. In some embodiments, in addition to, or instead of, using a calcium-free nuclear transfer medium, a calcium chelator may be used during and after nuclear transfer/cell fusion, and may be used until the oocyte is activated, or up to about one hour or two hours prior to activation. Suitable calcium chelators include, but are not limited to, ethylene diamine tetra-acetic acid (EDTA), ethylene glycol tetra-acetic acid (EGTA), 1,2-bis(o-aminophenoxy)ethane-N,N,N',N'-tetraacetic acid (BAPTA), and other calcium chelators known in the art. In some embodiments, a cell-permeant calcium chelator may be used, such as BAPTA-AM. For example, in one exemplary but non-limiting embodiment, BAPTA-AM may be used at a concentration of about 1-5 µM for up 20 minutes prior to nuclear transfer/cell fusion. The BAPTA-AM acts as an intracellular calcium chelator, thereby clamping the intracellular calcium concentrations during the nuclear transfer/cell fusion process. In some embodiments, in addition to, or instead of, using a calcium-free medium and/or a calcium chelator, one or more inhibitors of protein phosphatases can be used both during and after nuclear transfer/cell fusion, and may be used until the oocyte is activated, or up to about one hour or two hours prior to activation. Such protein phosphatases act downstream of calcium influx and can help to mitigate the effects of any calcium influx during the nuclear transfer/cell fusion process. Any suitable protein phosphatase known in the art may be used, including, but not limited to, okadaic acid.

Other exemplary nuclear transfer/cell fusion protocols are provided in the Summary of the Invention, Examples, and Claims of this application, and/or are known in the art, and may be used in conjunction with the present invention.

Activation of Reconstructed Oocytes and Subsequent Embryo Culture

As described elsewhere herein, the present invention provides various modifications and improvements to previously used somatic cell nuclear transfer techniques which allow human nuclear transfer embryos and human ES cell lines to be reliably obtained. Some of these improvements involve the step in which reconstructed oocytes are activated—after completion of the nuclear transfer/cell fusion step. In particular, in some embodiments the present invention provides improved methods that allow for the rapid and efficient activation of reconstructed oocytes and which lead to improved efficiencies of embryo generation and of ES cell line generation.

In some embodiments of the present invention the step of activating the reconstructed oocytes comprises delivering a calcium pulse to the reconstructed oocyte, for example using a calcium ionophore. Any suitable calcium ionophore may be used, including, but not limited to of A23187 and ionomycin. The calcium pulse may be repeated up to 10 times over the time course of 3 hours, or until the oocyte enters interphase. In such embodiments the reconstructed oocyte must be placed in a calcium-containing medium. Therefore, in embodiments where a calcium-free medium was used during the prior nuclear transfer/cell fusion step, the medium must be changed to a calcium-containing medium prior to, or concurrently with, contacting the oocyte with the calcium ionophore. In some such embodiments, the medium is changed to a calcium-containing medium about 15 minutes or about 30 minutes prior to contact with the calcium ionophore.

In some embodiments of the present invention the step of activating the reconstructed oocytes comprises contacting the oocyte with a translation inhibitor, or a meiotic kinase inhibitor, or, in some embodiments, both a translation inhibitor and a meiotic kinase inhibitor. Such methods promote entry into interphase. In some embodiments the translation inhibitor and/or meiotic kinase inhibitor may be used together with a calcium ionophore treatment, and may be used concurrently with the ionophore treatment and also after the ionophore treatment. Translation inhibitors and meiotic kinase inhibitors are known in the art and any suitable such agents can be used. Suitable translation inhibitors include, but are not limited to, puromycin. Suitable meiotic kinase inhibitors include, but are not limited to, 6-DMAP (the chemical names of "6-DMAP" include 6-(dimethylamino)purine and N6,N6-dimethyladenine, and 6-DMAP also has CAS registry number 938-55-6). Any concentration or amount of these agents that is sufficient to rapidly inhibit translation, rapidly inactivate meiotic kinases, and/or rapidly result in oocyte activation and entry into interphase may be used. For example, in one embodiment the translation inhibitor puromycin is used at approximately 10 µM and the meiotic kinase inhibitor 6-DMAP is used at approximately 2 mM. However, one of skill in the art can readily determine suitable concentrations or amounts of these or other agents to use using standard methods known in the art, such as dose-response studies and the like. Similarly, one of skill in the art can determine an appropriate duration for the exposure of the oocyte to such translation inhibitors and/or meiotic kinase inhibitors. In some embodiments of the present invention, the reconstructed oocyte is contacted with the translation inhibitor and/or the meiotic kinase inhibitor for approximately 4 to 4.5 hours.

In embodiments where the diploid human somatic cell genome is obtained by removing the nucleus or nuclear genome from a human somatic cell during the mitotic (M) stage of the cell cycle, a meiotic kinase inhibitor (such as 6-DMAP) need not be used. For example, the present inventors have found that under these circumstances, a reconstructed oocyte can be rapidly and efficiently activated by contacting it with medium containing a translation inhibitor (such as puromycin) for 4 hours without the addition of any meiotic kinase inhibitor (such as 6-DMAP)—as demonstrated by efficient polar body extrusion. However, in embodiments where the diploid human somatic cell nuclear genome is obtained by removing the nucleus or nuclear genome from a human somatic cell at some other stage of its cell cycle (such as during the G1 or G0 stages), it is preferred that both a translation inhibitor (such as puromycin) and a meiotic kinase inhibitor (such as 6-DMAP) be used.

Other exemplary activation protocols are provided in the Summary of the Invention, Examples, and Claims of this application. In addition, other methods that are known in the art to be useful for oocyte activation can be employed in conjunction with the methods described herein. For example, it is known in the art that oocyte activation can be achieved by applying an electric pulse to an oocyte, by chemically induced shock, by penetration of the oocyte by sperm, or by any combination of such methods. In some embodiments of the present invention the step of activating the oocyte may comprise one of such methods, such as, for example, administering an electrical pulse instead of, or in addition to, using a calcium ionophore. However, in other embodiments the present methods do not comprise using such other methods known in the art, such as using an electrical pulse.

Histone Deacetylase Inhibitors

As described elsewhere herein, one of the improvements over and above prior nuclear transfer techniques that is provided by the present invention is that the present methods result in improved reprogramming as a result of improved replication and segregation of the somatic cell genome in the activated oocyte. Chromosome mis-segregation is frequent after somatic cell nuclear transfer using other prior art methods. However, it is a discovery of the present invention that certain agents, when applied during the first cell cycle in the reconstructed oocyte, can increase the fidelity of chromosome duplication and enable efficient development of embryos to the blastocyst stage. Such agents include histone deacetylase inhibitors and histone methylation inhibitors.

Thus, in some embodiments the methods of the present invention involve contacting a reconstructed oocyte using one or more histone deacetylase inhibitors. Many histone deacetylase inhibitors are known in the art and any suitable histone deaceytlase inhibitor may be used in the methods of the invention. In some embodiments the histone deacetylase inhibitor is scriptaid (chemical name: 6-(1,3-Dioxo-1H,3H-benzo[de]isoquinolin-2-yl)-hexanoic acid hydroxyamide, CAS No-287383-59-9). In other embodiments the histone deacetylase inhibitor is Nch51 (chemical name: S-7-oxo-7-(4-phenylthiazol-2-ylamino)heptyl 2-methylpropanethioate, CAS No-848354-66-5). Other histone deacetylase inhibitors that may be suitable include, but are not limited to: m-carboxycinnamic acid bishydroxamide (CBHA), trichostatin A (TSA), trichostatin C, salicylihydroxamic acid (SBHA), azelaic bishydroxamic acid (ABHA), azelaic-1-hydroxamate-9-anilide (AAHA), 6-(3-chlorophenylureido) carpoic hydroxamic acid (3C1-UCHA), oxamflatin, A-161906, PXD-101, LAQ-824, CHAP, MW2796, MW2996, of SAHA, CI-994, PXD-101, LBH589, FK228, MGCD-0103, R306465, PCI-24781, SB-939, ITF-2357, and MS-275. In some embodiments the histone deacetylase inhibitor is selected from the group consisting of Scriptaid, Nch51 and trichostatin. In some embodiments both Scriptaid and Nch51 are used.

In some embodiments the methods of the present invention involve contacting a reconstructed oocyte using one or more histone methylation inhibitors. Many histone methylation inhibitors are known in the art and any suitable histone methylation inhibitor may be used in the methods of the invention. In one embodiment the histone methylation inhibitor is EPZ-6438. In one embodiment the histone methylation inhibitor is selected from the group consisting of EZH inhibitors, including deazaneplanocin A (DZNep), EPZ005687, or other compounds inhibiting PRC2, or the histone methyl transferase inhibitor BIX01294.

In some embodiments of the present invention a reconstructed oocyte is contacted with a histone deacetylase inhibitor and/or histone methylation inhibitor starting from the time of the first cell cycle in the reconstructed oocyte. In some embodiments, this may include contacting the reconstructed oocyte with the histone deacetylase inhibitor and/or histone methylation inhibitor during the activation step, or very soon after the activation step, or both during and after the activation step. In some embodiments the reconstructed oocyte, or embryo derived from the reconstructed oocyte, is contacted with the histone deacetylase inhibitor and/or histone methylation inhibitor for at least about 14 hours post activation, or for approximately 14 to approximately 21 hours post activation, or until just prior to the first mitosis. In some embodiments the reconstructed oocyte, or embryo derived from the reconstructed oocyte, is maintained in a medium that contains a histone deacetylase inhibitor and/or histone methylation inhibitor for at least 8 hours post activation. In some embodiments, the reconstructed oocyte, or embryo derived from the reconstructed oocyte, is maintained in a medium that contains a histone deacetylase inhibitor and/or histone methylation inhibitor for about 15 to about 20 hours post activation, or until before the first mitosis.

In some embodiments of the present invention, subsequent to the step of activating the reconstructed oocyte, the reconstructed oocyte is contacted with one or more histone deacetylase (HDAC) inhibitors and/or histone methylation inhibitors for approximately 4 to 4.5 hours, and is then subsequently cultured in the presence of one or more HDAC inhibitors and/or histone methylation inhibitors for an additional approximately 10-16 hours. In some embodiments, subsequent to the step of activating the reconstructed oocyte, the reconstructed oocyte is contacted with the histone deacetylase (HDAC) inhibitors Scriptaid and Nch51 for approximately 4 to 4.5 hours, and is then subsequently cultured in the present of the same HDAC inhibitors for an additional approximately 10-16 hours. In some embodiments the reconstructed oocyte is first activated (e.g., by contacting the oocyte with a calcium ionophore), and is then contacted with a medium comprising puromycin and a histodeacetylase inhibitor for about 4 hours, and is then contacted with a medium containing a histodeacetylase inhibitor but not puromycin for a further 11-17 (e.g., 11-13 or 15-17) hours. In some such embodiments the medium further comprises 6-DMAP.

Caffeine

In some embodiments the methods of the present invention comprise contacting the diploid human somatic cell genome, the enucleated human oocyte, the reconstructed oocyte, or the diploid human nuclear transfer embryo with caffeine.

In some embodiments the methods of the present invention do not comprise contacting the diploid human somatic cell genome, the enucleated human oocyte, the reconstructed oocyte, or the diploid human nuclear transfer embryo with caffeine. Rather, and as described in other sections of this patent application, the protocol is optimized at the level of taking steps to maintain membrane integrity and to limit the ability of calcium to compromise the meiotic arrest of the oocyte.

Micromanipulation and Culture of Oocytes, Somatic Cells & Embryos

Instruments for micromanipulating oocytes, somatic cells, karyoplasts, embryos and the like are well known in the art. Micropipettes and needles suitable for us in such manipulations include, but are not limited to, those available Origio, Humagen, Cook Medica, and Eppendorf Micropipettes can also be laboratory-made using a needle puller and a microforge. Any suitable micromanipulators for manipulating micropipettes can be used, such as those available from Narishige, Sutter Instruments, Eppendorf and other manufacturers. Manipulations can be performed using a microscope, such as an inverted microscope having a heated stage and equipped with any required micromanipulators. Suitable microscopes include, but are not limited to, the NikonTE2000-U equipped with a 40× objective and Hoffman contrast optics, and the Olympus IX71 with relief contrast optics. Other exemplary methods for micromanipulating oocytes, somatic cells, karyoplasts, embryos and the like are provided in the Examples of the present application and/or are known in the art.

In addition to some of the specific new methods described herein, several general methods suitable for handling of oocytes, somatic cells, karyoplasts, embryos and the like are well known in the art and can be used in conjunction with the specific methods of the present invention. For example, oocytes, somatic cells, and embryos can be handled and cultured or manipulated in physiologically suitable media known in the art. Generally oocytes, somatic cells, karyoplasts, and embryos will be maintained at 37° C. as far as is possible. For example, after oocyte retrieval (e.g., from a patient in an IVF clinic) and/or retrieval of somatic cells, such cells may be transported to the site of manipulation in a portable incubator at 37° C. Suitable media for culturing somatic cells are known in the art. Suitable media for culturing and manipulating oocytes are also known in the art. One such medium that may be used is named "GMOP-Splus" media, which is available from Vitrolife. Another suitable medium for embryo culture is Global media available from IVFOnline, LLC. In general, all manipulations should be performed in media that maintain a physiological environment at ambient atmosphere, while all culture should be performed in media that maintain a physiological environment in the atmosphere of an incubator—i.e., generally at 5% CO2. Media can be supplemented with a source of protein, e.g., human serum albumin or plasma without active complement factors (plasmanate). For example, Plasmanate, available from Talecris, may be added to Global media at 10% volume percentage. Other media that may be employed for manipulating oocytes includes, but is not limited to: HTF (IVFOnline, LLC or other supplier), Ham's F-10 or a modified version of it (Irvine Scientific), Gamete Buffer (Cook medical), or other media that maintain physiological conditions at ambient atmosphere. Maintenance and culture of oocytes, reconstructed oocytes and nuclear transfer embryos can also be performed using other commercially available media such as ART media (LifeGlobal or IVFOnline, LLC). Such media may be either single-step media (that can be used from day 1 to day 7), such as Global media, or the Single Step Medium from Irvine Scientific), or two-step media (that require a change on day 3 after activation). Examples of suitable two-step media systems include using Cook cleavage medium (from Cook Medical, Inc.) for day 1 to day 3 followed by Cook Blastocyst medium (from Cook Medical, Inc.) until day 7 post activation. Other two-step media systems include, but are not limited to, P-1 medium used with the MultiBlast Medium (from Irvine Scientific), and Quinn's Advantage Cleavage media used with Quinn's Advantage Blastocyst media (Cooper Surgical). Embryos can be cultured using any suitable means known in the art. For example, they may be cultured in small drops (e.g., around 30-50 microliters) of media, which may be covered with oil. Suitable oils that can be used include "oil for embryo culture" from Irvine Scientific, "culture oil" from Cook Medical, and "LiteOil" from IVFOnline. Embryos may also be cultured in small dishes or wells, such as 4-well cell culture plates (e.g., from Thermo Scientific) containing around 500 to 700 microliters of medium. When this method is used there may be no need to cover the cultures with oil because of the larger liquid volume.

Other exemplary methods, reagents and media for handling and culture of oocytes, somatic cells, and embryos are provided elsewhere in this Detailed Description, and/or in the Summary of the Invention, Examples, and Claims sections of this patent application. For example, in some embodiments activated oocytes/embryos are cultured in Global total medium containing 10% FBS (quality controlled for compatibility with human ES cell growth) and an HDAC inhibitor for 12 hours, followed by culture to the blastocysts stage in medium containing 10% FBS.

Derivation of Pluripotent Stem Cells

Methods for obtaining pluripotent embryonic stem cells (ES cells) from blastocyst stage embryos are known in the art, and any such suitable method may be used in accordance with the present invention. For example, in one embodiment the nuclear transfer embryos of the present invention are cultured until an inner cell mass of an embryo may be isolated after approximately six to seven days of development, or until the embryo has reached the expanded blastocyst stage. Pluripotent stem cells can be generated from such an inner cell mass, for example using methods known in the art. Analysis of gene expression and developmental potential can also be performed to demonstrate the pluripotency of the cells obtained, and karyotype and short tandem repeat analysis can be performed to confirm the presence of the somatic cell genome in the stem cells. In some embodiments the inner cell mass of a blastocyst may be isolated using a laser. In some embodiments it may also be possible to obtain pluripotent stem cells without isolation of the inner cell mass, for example by plating an intact blastocyst in a dish. In some embodiments the inner cell mass of a blastocyst may be plated on a layer of suitable feeder cells, including, but not limited to, a feeder layer of mouse embryonic fibroblast cells. The feeder layer may also be composed of human cells, or any other suitable substrate that can support the growth of human pluripotent stem cells. Such substrates include, but are not limited to, Matrigel, UV/ozone treated plasticware, gelatin-coated plastic, and the like. Any culture medium suitable for culture of pluripotent stem cells may be used, and several such media are known in the art. For example, the culture medium may be composed of Knockout DMEM, 20% Knockout Serum Replacement, nonessential amino acids, 2.5% FBS, Glutamax, beta-mercaptoethanol, 10 ng/microliter bFGF, and antibiotic. The employed medium may also be a variation of this medium, for example without the 2.5% FBS, or with a higher or lower % of knockout serum replacement, or without antibiotic. The employed medium may also be any other suitable medium that supports the growth of human pluripotent stem cells in undifferentiated conditions, such as mTeSR (available from STEMCELL Technologies), or Nutristem (available from Stemgent), or ES medium, or any other suitable medium known in the art. Other exemplary methods for generating/obtaining pluripotent stem cells from a blastocyst, such as a blastocyst made according to the methods of the present invention, are provided in the Summary of the Invention, Examples, and Claims of this application, and/or are known in the art.

Kits

In some embodiments the present invention provides kits comprising components and compositions useful in performing nuclear transfer methods. Such kits, and the components and compositions they contain, were invented in the course of developing the improved human somatic cell nuclear transfer protocols described herein. However, such kits, and the components and compositions they contain, may also be useful in other nuclear transfer applications, such as in protocols for nuclear transfer using non-human cells and in protocols for nuclear transfer using non-somatic cells, such as oocyte nuclear transfer protocols. Kits according to the present invention may comprise any of the components or compositions described herein in any desired combination.

For example, in one embodiment the present invention provides a kit for use in a nuclear transfer method, the kit comprising one or more (or two or more, or three or more, or four or more) of the following components: (a) a nuclear transfer/cell fusion component (wherein the nuclear transfer/cell fusion component comprises a calcium free medium, a calcium chelator, a protein phosphtase inhibitor, and/or a fusogenic agent), (b) an activation component (wherein the activation component comprises one or more of a calcium ionophore, a protein translation inhibitor, and a meiotic kinase inhibitor), (c) an embryo culture component (wherein the embryo culture component comprises one or more of a histone deacetylase inhibitor, a histone methylation inhibitor, a protein translation inhibitor, and a meiotic kinase inhibitor), and (d) an ES cell derivation component (wherein the ES cell derivation component comprises fetal bovine serum (FBS)).

In some such embodiments one or more of the "components" may be a medium, such as a nuclear transfer/cell fusion medium, an activation medium, an embryo culture medium, and/or an ES cell derivation medium.

The invention is further described by way of the following non-limiting examples.

EXAMPLES

Certain publications are referred to throughout the Examples section of this patent application. In some sections of the Examples the publications are referred to by reference to the first author's name and the publication year (shown in parentheses). In other sections of the Examples the publications are referred to using numerals (shown in superscript) which refer to numbered publications. In both cases the full citations for each of publications referred to are provided in the Reference List located at the end of the Examples.

Example 1

Human pluripotent stem cells have the ability to self-renew indefinitely, and give rise to cell and tissue types of all three germ layers, enabling the study of human disease in cellular models (for review see (Robinton and Daley, 2012)). More recently, human embryonic stem cells have been approved for use in clinical trials aimed at determining the safety of transplanted cells in spinal cord injury and macular degeneration (Schwartz et al., 2012). The derivation of pluripotent stem cells from somatic cells holds the promise to use autologous cells for cell replacement for degenerative diseases such as diabetes or Parkinson's Disease (Tabar et al., 2008).

The transfer of somatic cell nuclei into oocytes can give rise to pluripotent stem cells that are consistently equivalent to embryonic stem cells[1-3], holding promise for autologous cell replacement therapy[4,5]. Though methods to induce pluripotent stem cells from somatic cells by transcription factors[6] are widely used in basic research, numerous differences to embryonic stem cells have been reported[7-11], potentially affecting their clinical use. Because of the therapeutic potential of diploid embryonic stem cell lines developed from adult cells of diseased human subjects, we have systematically investigated the parameters affecting efficiency and developmental potential in their derivation.

Results

Nuclear transfer using an efficient activation protocol and HDAC inhibitors during the first cell cycle allow development to the blastocyst stage.

Figures 2A, 2B, 2C:
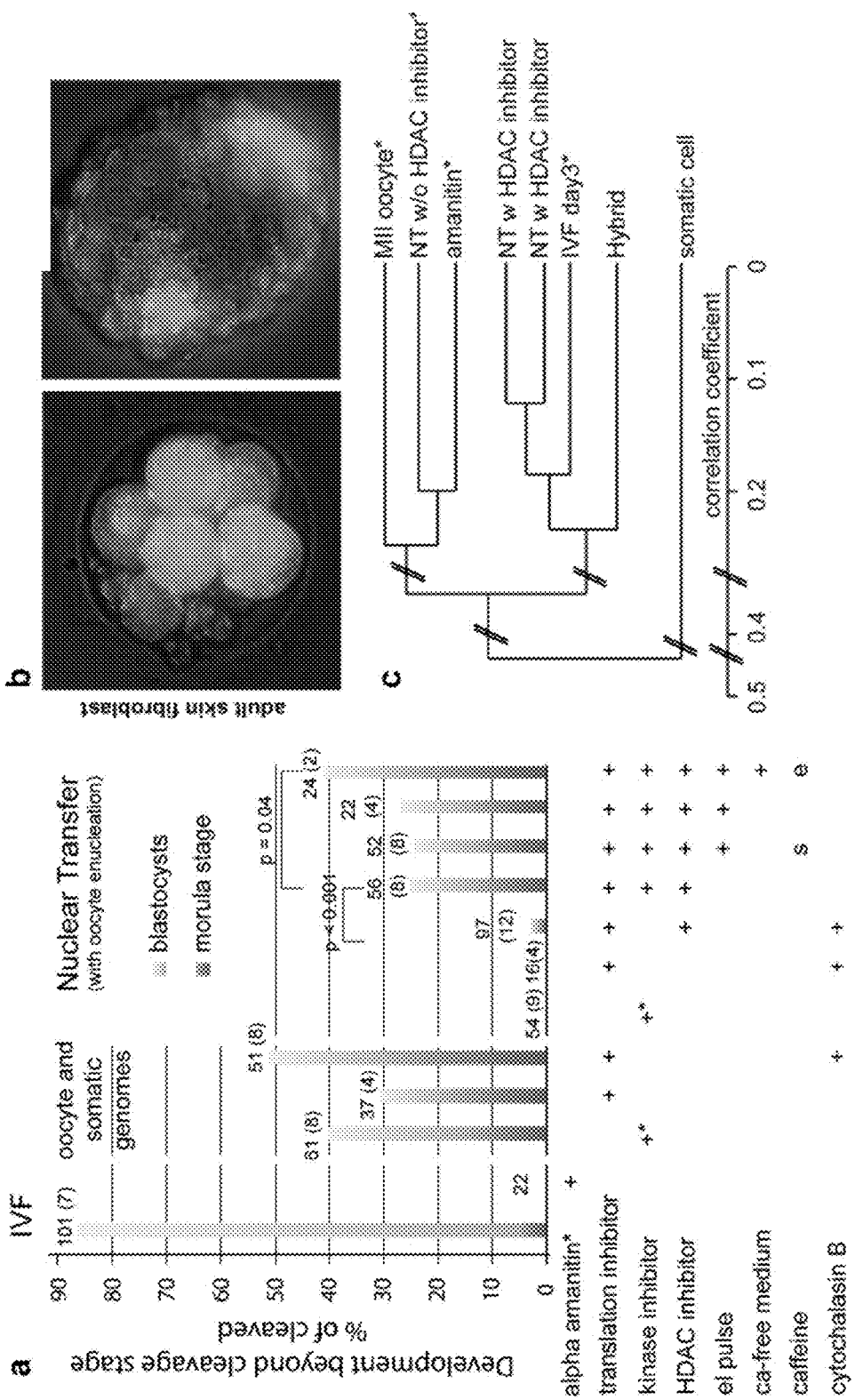
FIGS. 2A-2C |Developmental potential of somatic cell nuclear transfer oocytes. a, percentage of cleaved oocytes developing beyond the cleavage stage. The total number of oocytes and the number of ooycte donors (in parenthesis) contributing to a particular experiment is indicated above each column. S=short treatment during the manipulation as in13, e=extended treatment, including during oocyte transport. b, expression of a GFP transgene contained in the genome of the adult skin fibroblast used for transfer, at the cleavage stage and at the blastocyst stage. c, Cluster analysis of global gene expression profile after nuclear transfer of adult somatic cells, as well as oocytes and IVF embryos. *Data are from previous publications14 and 36 (see Reference List) and serve for comparison to the new conditions.
Figures 3A, 3B, 3C:
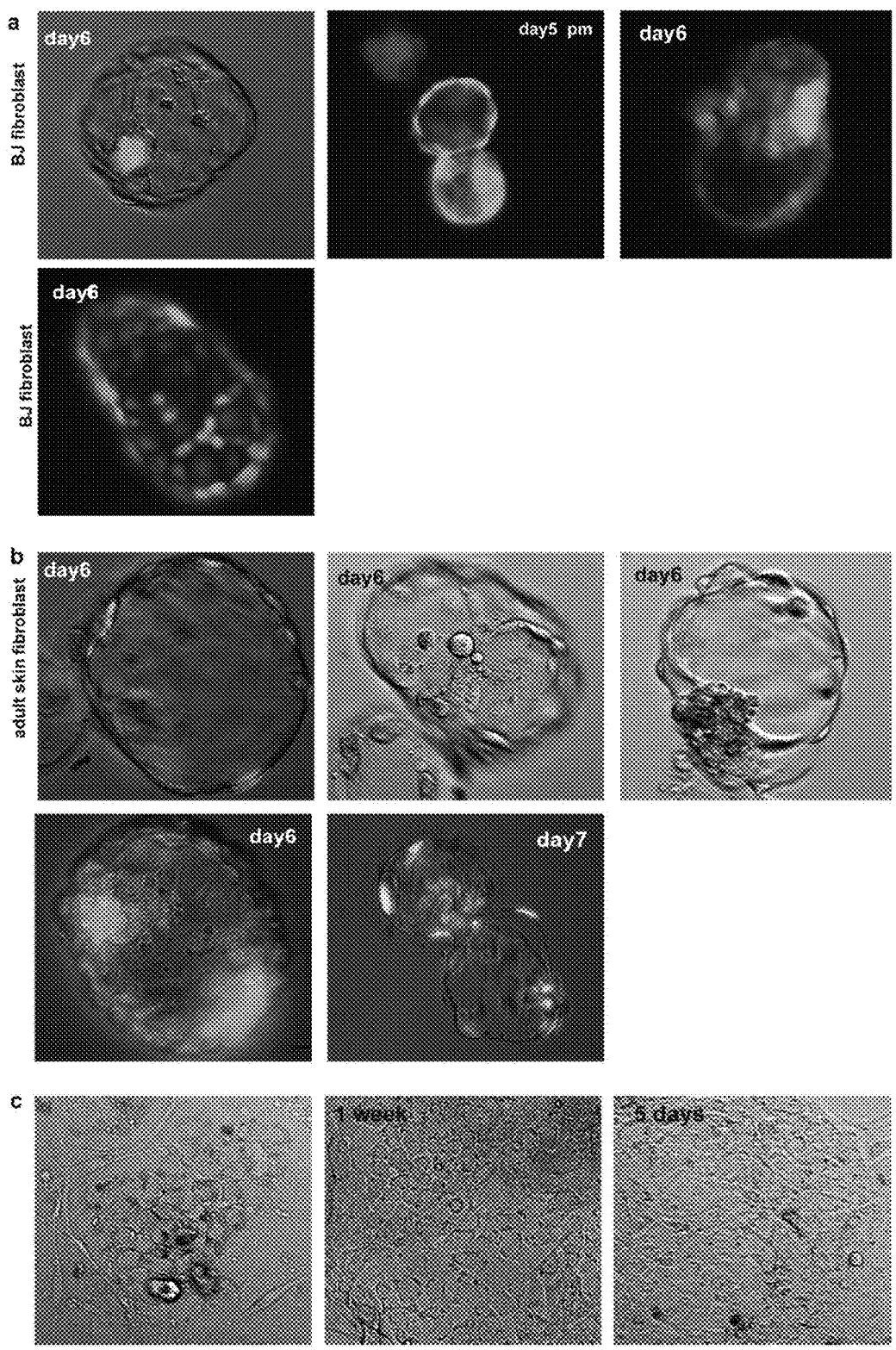
FIGS. 3A-3C |Development to the blastocyst stage and transcriptional activation of the transferred genome a, Blastocyst derived after nuclear transfer of a BJ fibroblast genome (neonatal foreskin fibroblasts). b, Blastocysts derived after nuclear transfer of an adult skin fibroblast genome. c, ES cell outgrowth. Time post blastocyst plating is indicated.

We have previously reported the derivation of triploid pluripotent stem cells containing a reprogrammed somatic cell nucleus, and a haploid oocyte genome[14]. Development to the blastocyst stage only occurred in the presence of the oocyte genome. Diploid nuclear transfer cells arrested development at the cleavage stages, failing to express embryonic genes[14]. To improve developmental potential of diploid nuclear transfer oocytes, we tested the effect of histone deacetylation inhibitors as well as changes to the artificial activation protocol on developmental potential after nuclear transfer of neonatal and adult somatic cells. These modifications were based on the report that deacetylase inhibitors improve reprogramming efficiency and development after somatic cell nuclear transfer into mouse oocytes[15], and on our previous observation that parthenogenesis was more efficient when oocytes were activated with the translation inhibitor puromycin[16] than when activated with the kinase inhibitor 6-dimethylaminopurine (6-dmap)[14] (FIG. 1). We first tested the use of puromycin for oocyte activation for somatic cell nuclear transfer without removing the ooycte genome, resulting in efficient development to the blastocyst stage (FIG. 2A). However, when this activation protocol was applied to enucleated oocytes, development still arrested at cleavage stages (FIG. 1A). Only when we applied the histone deacetylation inhibitor (HDAC) scriptaid for the first 17 hours of embryo culture after the calcium pulse, did we observe development to the morula and blastocyst stage at a low frequency (FIG. 2A). An additional improvement in developmental potential was observed when both puromycin and 6-DMAP were combined during oocyte activation, resulting in development to expanded blastocysts (FIG. 2A, 2B, FIG. 3A, 3B). Puromycin promotes ooyce activation by inhibition of translation of cyclinB[17,18], while 6-DMAP inhibits the activity of meiotic kinases; their combined use may result in a more complete or more rapid inactivation of meiotic kinases. These results show that an improved activation protocol using both puromycin and 6-DMAP for kinase inhibition and the use of scriptaid allowed development to the blastocyst stage after somatic cell nuclear transfer.

Reprogramming of Gene Expression after Somatic Cell Nuclear Transfer

Because development beyond the cleavage stage requires gene expression[19], development of nuclear transfer oocytes to the morula and blastocyst stage indicates transcriptional activity of the transferred somatic cell genome. The use of somatic cells containing a GFP transgene allowed us to conveniently visualize the activity of the somatic cell genome. While nuclear transfer protocols that did not result in development beyond the cleavage stage showed no expression of the GFP transgene[14], 58% (14 of 24) of the nuclear transfer cells treated with histone deacetylation inhibitor showed GFP expression (FIG. 2B), and had a global gene expression profile similar to IVF embryos (FIG. 2C), demonstrating that transcriptional reprogramming had occurred. From the 7 blastocysts obtained using optimized nuclear transfer protocols, we attempted to derive nuclear transfer ES cells. 3 of the blastocysts formed an outgrowth (FIG. 3C), but none gave rise to an ES cell line.

More recently, it has become possible to derive diploid pluripotent stem cell lines from fetal fibroblasts[13]. The derivation of two cell lines from neonatal fibroblasts was also mentioned, although no karyotype or evidence of pluripotency was provided. Thus far, there is no report on the derivation of nuclear transfer ES cell lines from any postnatal cell. While the use of the HDAC inhibitor TSA is consistent with our approach, the authors also attributed successful derivation to the use of caffeine during oocyte enucleation to promote nuclear envelope breakdown and chromosome condensation, the use of a hormone stimulation protocol yielding a small number of high quality oocytes, and to the use of an electrical pulse for oocyte activation. Because these conclusions are based on a limited number of donors and on the use of fetal fibroblasts[13], we determined the relevance of these modifications on the derivation of pluripotent embryonic stem cells after nuclear transfer of postnatal and adult somatic cells.

Maintaining Plasma Membrane Integrity

Figures 4A, 4B, 4C, 4D, 4E, 4F, 4G, 4H:
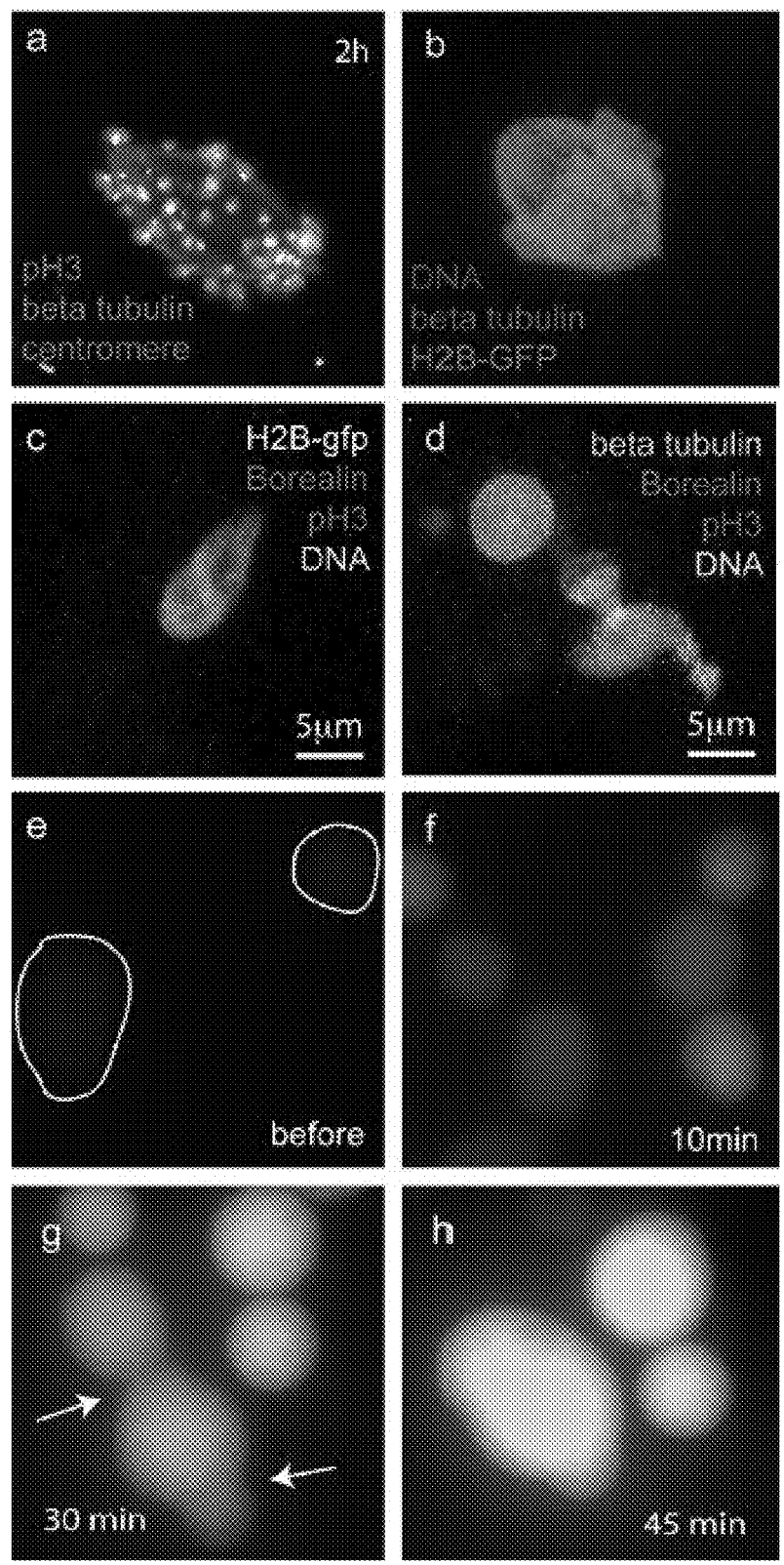
FIGS. 4A-4H |Chromosome condensation and spindle assembly after somatic cell nuclear transfer. a, Spindle assembly on a somatic G1/G0 genome. Time indicates hours post transfer. pH3, phosphorylated histone H3. b, Spindle of the human MII oocyte. c, Somatic genome in an oocyte that failed to assemble a birefringent spindle around somatic chromatin. The somatic genome was transferred using undiluted Sendai virus. Note the lack of phosphorylated histone H3. d, Oocyte genome in the same egg. Note the segregation of oocyte chromosomes. e-h, Fluorescence of the calcium indicator dye fluo-4 in oocyte karyoplasts before and after incubation with fusogenic Sendai virus (less than 20 s). Time after exposure is indicated. Arrows point to sites of fusion.

We first determined whether oocyte enucleation interfered with the ability of the oocyte to condense somatic chromatin, a process correlating with developmental potential after somatic cell nuclear transfer[20]. When we transferred somatic cell genomes at G1 or G0 stages of the cell cycle into enucleated oocytes, 17 of 23 (74%) assembled a spindle within 1-4 hours after transfer as determined by microtubule birefringence[21] or immunostaining (FIG. 4A). Somatic chromosomes were condensed and phosphorylated on serine28 of histone H3, but not aligned on a metaphase plate, because bipolar amphitelic attachments cannot occur on unreplicated chromosomes, as they do in a spindle of the MII oocyte (FIG. 4B). Though chromosome condensation did not occur in all oocytes that were enucleated and transferred with a somatic cell genome, failure to condense somatic chromatin was not related to the enucleation procedure. Chromosome condensation and spindle assembly occurred with similar efficiency in oocytes only transferred with a somatic cell genome and not enucleated ($10/13$, 77%). Two non-enucleated oocytes that had failed to assemble a spindle around somatic chromatin were analyzed using immunochemistry. Both oocytes showed no phosphorylation of somatic histones (FIG. 4C), and showed segregation of the oocyte genome with the formation of a midbody positive for borealin (FIG. 4D), a component of the chromosome passenger complex localizing to the midbody at anaphase[22]. In contrast to a previous report using a small number of 3 enucleated oocytes[13], an effect of oocyte enucleation on meiotic arrest was not apparent.

Figures 5A, 5B:
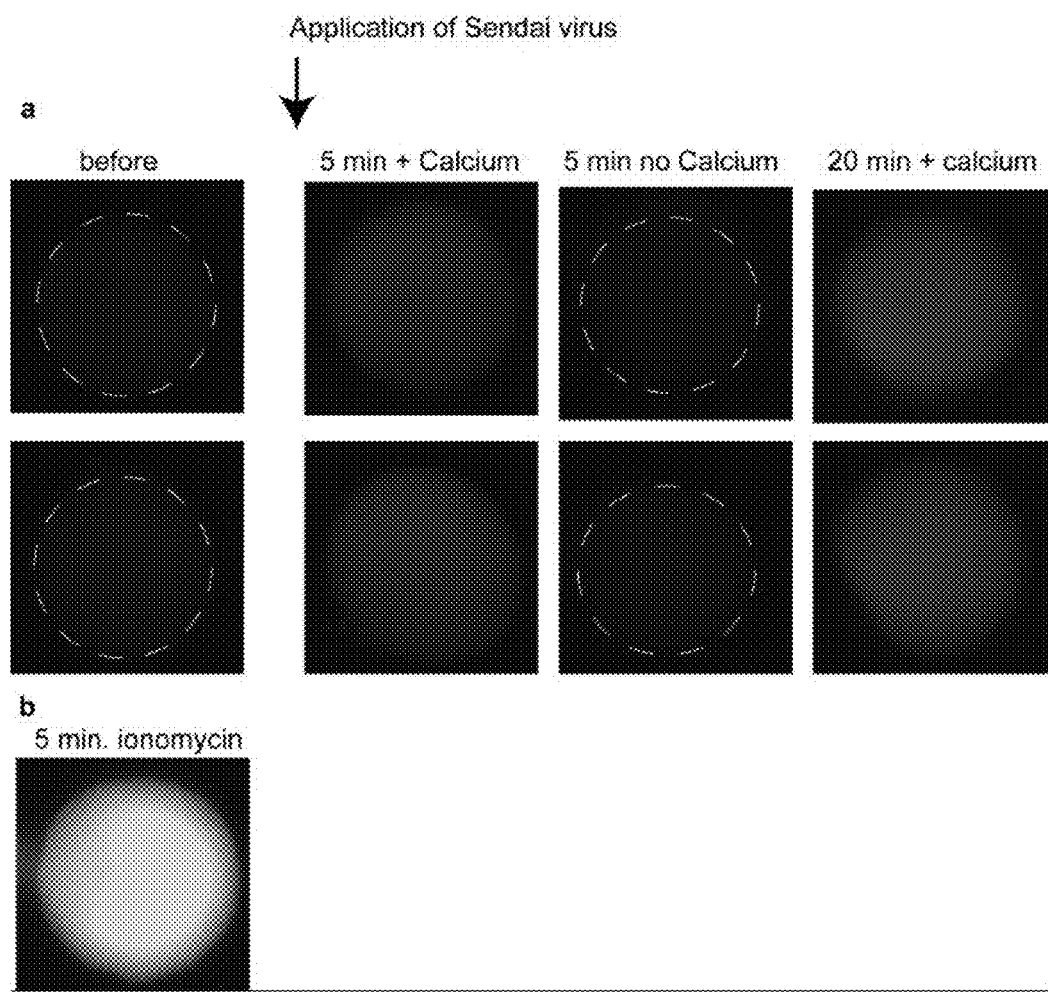
FIGS. 5A-5B |Fluorescence imaging with the calcium-responsive dye fluo-4. a, Human oocytes were incubated in medium containing fluo-4 for 30 minutes, imaged for fluorescence, and concentrated Sendai virus was added below the plasma membrane. Shown are two oocytes for each condition or time point. Note that in the absence of calcium in the medium, fluorescence did not increase, while a small increase in fluorescence appears to occur in calcium-containing medium. Time point after addition of the virus is indicated. b, incubation of a human oocyte in 3 µM of the calcium ionophore ionomycin as a positive control.
Figures 6A, 6B:
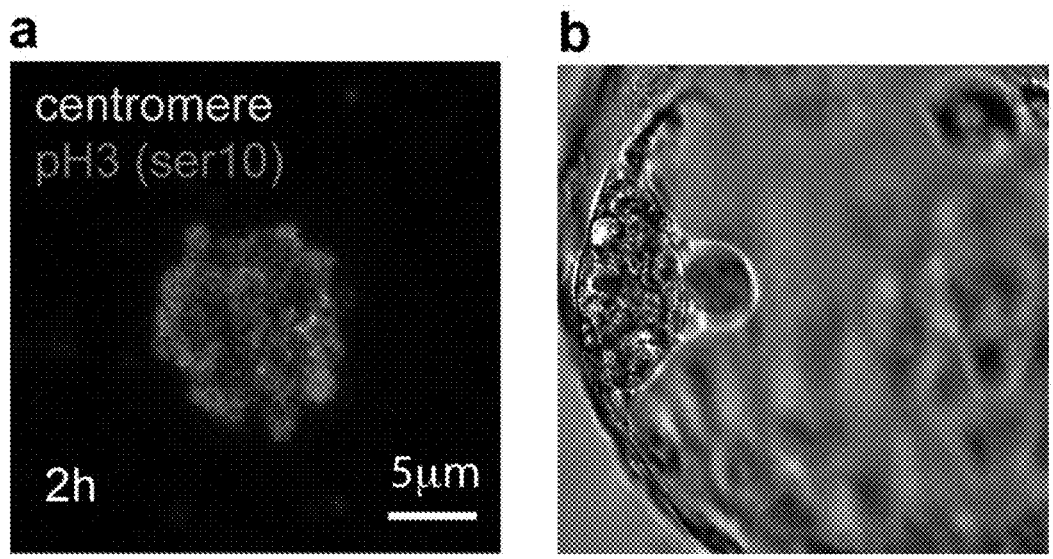
FIGS. 6A-6B |Somatic cell nuclear transfer in the absence of calcium. a, Immunochemistry to determine chromosome condensation and histone phosphorylation after transfer of a somatic cell at interphase. b, High quality blastocysts obtained after nuclear transfer with the manipulations conducted in the absence of calcium.

Because a rise in intracellular calcium concentration is a potent inducer of anaphase in human oocytes, we investigated the effect of Sendai virus on intracellular calcium levels. During enucleation of the oocyte, the genome was removed as a karyoplast, surrounded by a small amount of cytoplasm and plasma membrane. Intact oocytes and karyoplasts were equilibrated with the calcium indicator dye fluo-4 and exposed to inactivated Sendai virus. Within minutes, an increase of fluo-4 fluorescence was observed (FIG. 4E-4H, FIG. 5). Fluorescence was calcium dependent, as oocytes incubated in calcium-free media showed decreased fluo-4 fluorescence compared to oocytes incubated in calcium-rich media (FIG. 5). These results show that the fusion of somatic cells using Sendai virus can increase calcium influx and compromise the integrity of meiotic arrest. For these reasons, nuclear transfer experiments from all but 4 oocyte donations were performed using Sendai virus diluted up to 20 fold. And for two donations, calcium was omitted from the medium used for transfer, as well as during incubation prior to oocyte activation. This manipulation in the absence of calcium was compatible with condensation of transferred somatic chromatin (FIG. 6A).

Additional technical adaptations, including an electrical pulse for oocyte activation and the use of caffeine during oocyte manipulation allowed development to the blastocyst stage, consistent with a previous report[13], though the efficiency remained at a modest 10% blastocyst development. The most efficient and high quality blastocyts were obtained when caffeine was also added during oocyte transport, combined with omitting calcium from the manipulation medium (FIG. 2A), with blastocysts of high quality with a distinct inner cell mass and expanding trophectoderm (FIG. 6B).

Figures 7A, 7B:
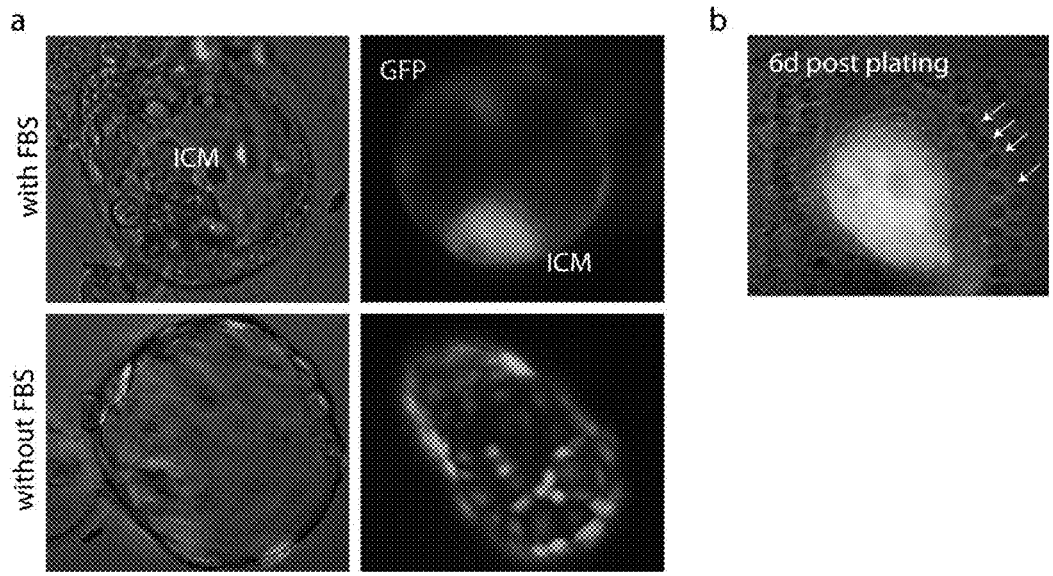
FIGS. 7A-7B |Effect of FBS on blastocyst morphology and ES cell derivation. a, Blastocyst generated by somatic cell nuclear transfer in the presence or absence of FBS. b, ICM 6 days post plating. Arrows point to laser marks used to ablate the remaining trophectoderm cells.
Figure 9:
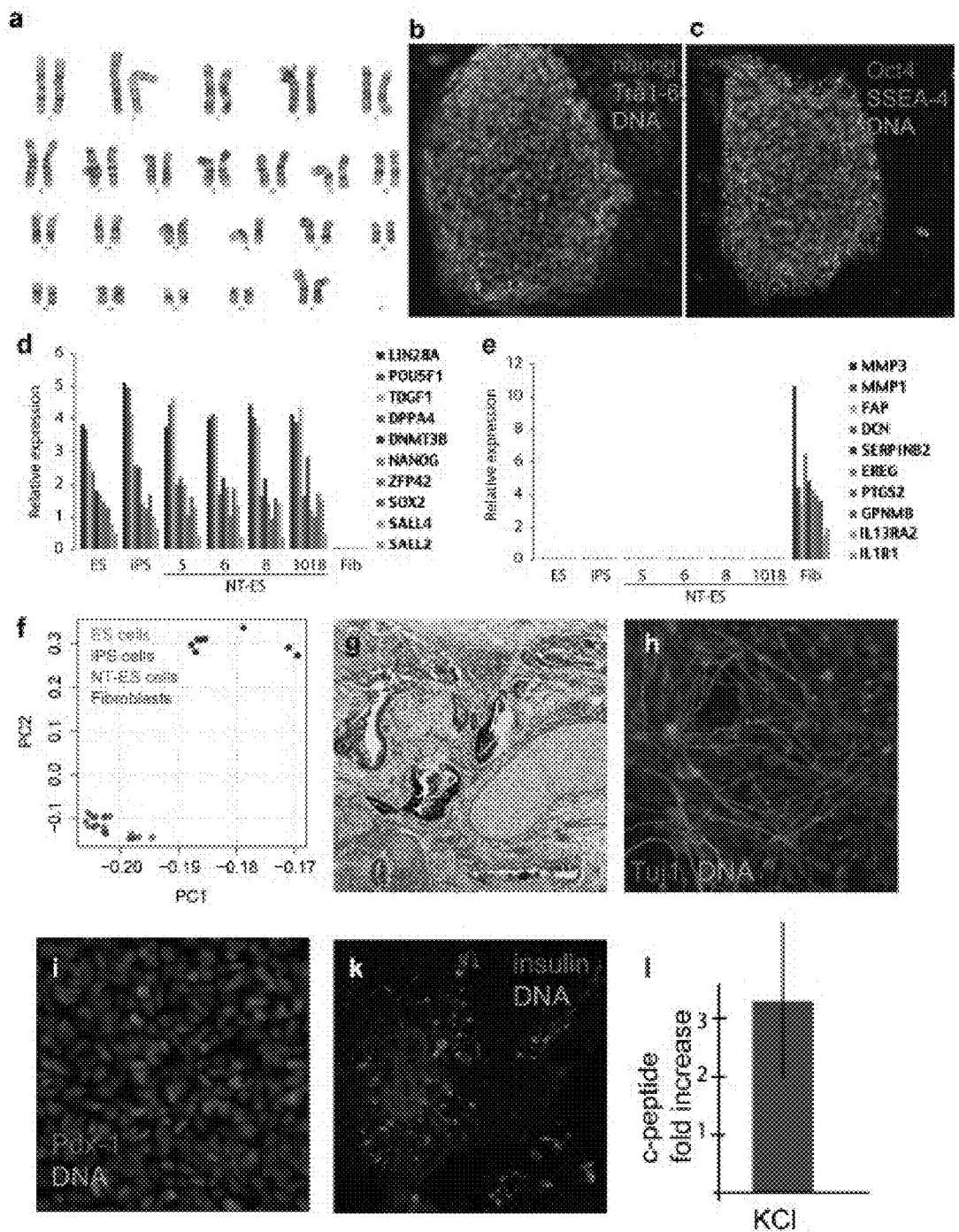
FIGS. 9A-9I, 9K-9L |Derivation of diploid NT-ES cells from neonatal and adult somatic cells. a-c Characterization of an NT-ES cell line from adult somatic cells of a female type 1 diabetic (ID 1018) a, karyotype, b,c, expression of pluripotency markers. d-f microarray analysis in dermal fibroblasts, and NT-ES cell lines NT-ES5, NT-ES6, NT-ES8 and NT-ES 1018, and in ES and iPS cells. d, Expression of pluripotency markers. e, expression of fibroblast specific genes. f, Principle component (PC) analysis of global gene expression patterns of NT-ES cells, ES cells from normally fertilized embryos, iPS cells and fibroblasts. g, Teratoma analysis, h, directed differentiation into neurons according to34. i, Directed differentiation into pancreatic precursor cells and insulin producing cells, k, that are able to secrete insulin into the medium upon stimulation with potassium,1, according to reference 33.
Figure 10:
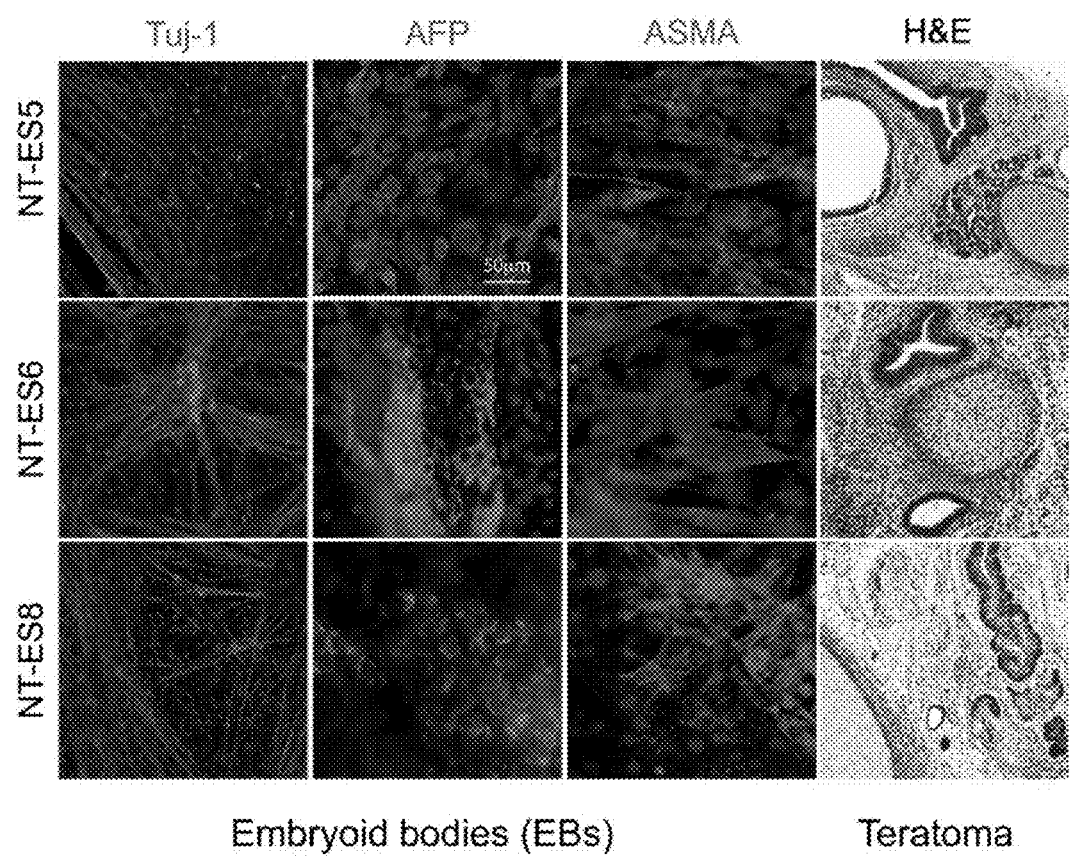
FIG. 10 |Differentiation of NT-ES cell lines made from male foreskin BJ fibroblasts in embryoid bodies and in teratomas.

Derivation of Diploid Nuclear Transfer ES cells from Adult and Neonatal Somatic Cells For the derivation of nuclear transfer ES (NT-ES) cell lines, we also added fetal bovine serum (FBS) to the embryo culture and derivation media[13]. FBS promoted the formation of an inner cell mass (ICM) at the expense of trophectoderm cells. Of 8 nuclear transfer blastocysts generated without the addition of FBS, 2 lacked an ICM, and contained exclusively (60 or more) trophectoderm cells (FIG. 3). In the presence of FBS, even embryos with a small number of cells formed a distinct inner cell mass (4 of 4), with fewer than 20 trophectoderm cells (FIG. 7A). Three of four such blastocysts formed an outgrowth (FIG. 10B) and developed into three cell lines containing a diploid male karyotype derived from foreskin fibroblasts (FIG. 8). An NT-ES cell line with a diploid female karyotype was derived from an adult somatic cell of a type 1 diabetic (age 32 years), (FIG. 9A). All four cell lines expressed markers of pluripotency (FIG. 9B-9D, FIG. 8), and lacked markers of the dermal fibroblasts (FIG. 9E). In an analysis of global gene expression patterns, NT-ES cells clustered closely with other human pluripotent stem cells, including ES cells from fertilized embryos and induced pluripotent stem (iPS) cells (FIG. 9F). In embryoid bodies and upon transplantation into immuno-compromised mice, all four NT-ES cell lines gave rise to cell types of three germ layers (FIG. 9G, FIG. 10). When exposing them to a combination of patterning factors (Methods) we found efficient differentiation into neurons (FIG. 9H), pancreatic and duodenal homeobox-1 (Pdx-1) positive pancreatic cells (FIG. 9I), and into insulin positive cells (FIG. 9K) that were able to secrete insulin into the medium upon potassium stimulation (FIG. 9L).

Discussion

Figures 11A, 11B, 11C, 11D:
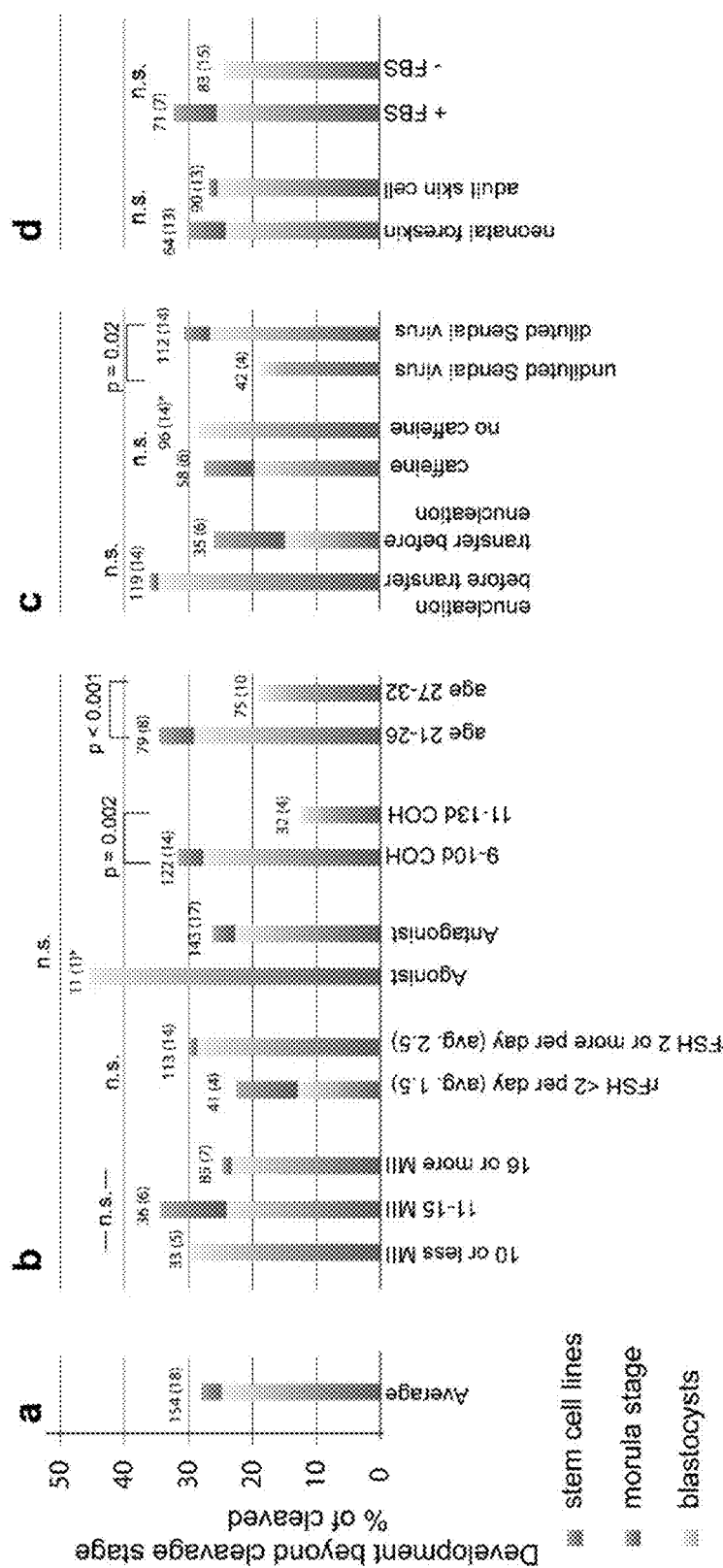
FIGS. 11A-11D |Retrospective analysis of the developmental potential of nuclear transfer oocytes. Shown is the percentage of oocytes developing beyond the cleavage stage, as percentage of eggs progressing beyond the 1-cell stage. Because oocytes of a donor were used to compare two different conditions, if for a particular comparison the added number of oocyte donors exceeds 18, it indicates that these conditions were tested in parallel using oocytes of the same donor. The total number of oocytes used for analysis remained constant. a, average of the 154 oocytes of 18 donors. The total number of 154 oocytes is not equal to the number of oocytes donated by the 18 donors, but is the number of oocytes used for the study of developmental potential after somatic cell nuclear transfer. b, Analysis with regard to factors relevant to the hormonal treatment of oocyte donor. c, Factors relevant to the manipulation. d, Analysis regarding cell source and use of FBS for culture. n.s, non significant. Statistical analysis using Chi-square test was performed by comparing the total number of cells formed in each condition. Morulas were assigned 15 cells, blastocysts or blastocysts that gave rise to stem cell lines 30 cells, reflecting the estimated minimal cell count for each group.

Though nuclear transfer blastocysts could be obtained with an efficiency of approx. 10%, developmental efficiency varied between different oocyte donors, even when other aspects of the nuclear transfer protocol were kept constant. In an experiment of 3 oocyte donations occurring in short succession within 4 days, we used identical protocols, reagents, and replicates of the same somatic cell cultures. Oocytes of one donor yielded blastocysts with an efficiency of 44% (4/9 oocytes), another yielded cleavage stage cells only, and oocytes of a third donor resulted in a single blastocyst (1/12 oocytes, 8%). To better understand the source of this variation we performed a retrospective analysis of variations in the hormone stimulation protocol and in nuclear transfer procedures (FIG. 13) examining 154 oocytes obtained from 18 donors (oocytes in the last four columns of FIG. 2A). In contrast to a previous report[13], we found no effect of the number of MII oocytes retrieved per donation and developmental competence (FIG. 11B). In fact, the derivation of a NT-ES cell line from adult somatic cells resulted using 9 oocytes for nuclear transfer of a cycle with a total of 31MII oocytes. We also observed no significant effect of the daily dose of gonadotropin. And both gonadotropin releasing hormone (GnRH) antagonist and GnRH agonist protocols resulted in development to the blastocyst stage with a similar efficiency. However, a trend towards a negative effect of the total duration (days) of gonadotropin stimulation required to reach a follicular size of 18 mm, was observed. In addition, greater developmental potential in the age group of 21-26 years in comparison to age 27-32 years was noted. Though short stimulation cycles are preferred during in vitro fertilization (IVF) treatments[23], no significant effect on blastulation have been demonstrated. And although an effect of maternal age on pregnancy rates is well documented, a decrease in blastulation was shown above the age of 40[24]. The requirements for somatic cell reprogramming using the currently available nuclear transfer protocols may be more stringent, and reveal biological differences that are not readily apparent in IVF.

Our previous studies had shown that the removal of the oocyte genome reduced developmental potential[14]. Tachibana and colleagues suggested that this may be because the removal of the oocyte genome compromises the meiotic state, condensation of somatic chromatin, thereby affecting embryonic development. However, we found that chromosome condensation occurs at a similar frequency in enucleated and nucleated oocytes. We also found no difference in developmental potential if the somatic genome was transferred 30 min before or after the removal of the oocyte genome (FIG. 11D). Instead, our data point to cell fusion as a cause for a compromised meiotic state observed after nuclear transfer. Fusion acts by compromising plasma membrane integrity, and can thereby lead to an increase in intracellular calcium levels and failure to condense somatic chromatin (FIG. 4). The use of low concentrations of fusogenic Sendai virus and calcium-free media during cell fusion improved developmental potential and allowed derivation of stems from adult somatic cells (FIG. 2A, FIG. 11C). Therefore, a likely interpretation of our previous observations is that the retention of the oocyte genome promotes developmental potential by compensating for inefficient reprogramming of the transferred somatic genome. Improvements in the nuclear transfer protocol remove this requirement of the oocyte genome for development after nuclear transfer. Future studies should lead to a better understanding of the molecular mechanisms how these technical improvements affect reprogramming and developmental outcome.

In summary, we have demonstrated the derivation of human ES cells from adult somatic cells by nuclear transfer. The stem cells are pluripotent and could be differentiated into insulin producing beta cells, the cell type lost in patients with type 1 diabetes. Thus, somatic cell nuclear transfer may be a useful strategy to generate cells for therapeutic cell replacement, a concept demonstrated in proof of principle experiments in immunodeficient[5] and in parkinsonian mice[4]. Though it is now possible to induce stem cell formation by overexpression of transcription factors[6], these cells often are differentiation defective', contain aberrant patterns of cytosine methylation[9,10,25] and hydroxymethylation[8], somatic coding mutations[26], and show biallelic expression of imprinted genes[11]. Studies comparing isogenic nuclear transfer ES cells to iPS cells generated from the same somatic cell cultures should enable evaluating the quality of cells generated by different methods of reprogramming.

Materials and Methods

Oocyte Donors

Oocytes were obtained as previously reported[14,16]. In brief, oocyte donors were recruited from an oocyte donation program. Potential participants discussed the research with a physician and were offered study participation. Upon choosing to donate for research, subjects gave signed informed consent for the study protocol and the use of their oocytes in nuclear transfer research. During a period of three years and four months, 35 subjects donated a total of 512 mature MII oocytes, (average=14.63 oocytes/cycle, range=2-31 oocytes/cycle). 423 of these oocytes were used for developmental analyses after somatic cell nuclear transfer reported here. 6 of the donors had one or more previous pregnancies, and 5 had previously donated for reproductive purposes. There were no repeat donations for this study.

Both GnRH antagonist (n=33) and GnRH agonist (n=2) protocols were used. The GnRH antagonist protocol was performed by administering daily subcutaneous rFSH (recombinant follicle stimulating hormone) injections starting on day 2 of the menstrual cycle and the addition of daily GnRH antagonist (Ganirelix) starting on day 6 of stimulation. Final oocyte maturation was triggered after reaching a follicle size of 18 mm with 4 mg GnRH agonist (Lupron) and 1000IU hCG (human chorionic gonadotropin, Novarel).

The GnRH agonist protocol was performed by administering daily GnRH agonist for at least 14 days followed by daily rFHS injections. Final maturation trigger was performed by administering 10,000IU hCG.

For both agonist and antagonist protocols, the dose of rFSH generally consisted of 2 ampules a day (range 1-3, average 2.49) and the time of stimulation was 10 days (range 9-13 days, average 10.29). Initial dose was established clinically based on subject age, baseline antral follicle count, and anti-mullerian substance (AMH) level. Dose adjustments and the total days of stimulation were adjusted individually based on follicle number and size and serum estradiol (E2) levels. Hormones were administered by clinical staff, to ensure consistent application. At the time of oocyte retrival, venipuncture was performed for DNA isolation. All human subjects' research was reviewed by an institutional review board and stem cell committees.

Oocyte Manipulations

Oocytes were enucleated using microtubule birefringence (Oosight) as described previously by Noggle et al., 2011. Nuclear transfer was performed by fusion of somatic cells to oocytes using inactivated Sendai virus diluted 1:10 to 1:20 in suspension medium. Fusion was confirmed visually. 1-3 hours post fusion, oocytes were activated using 3 μM ionomycin in Global total for 5 minutes at 37 degrees celsius, followed by culture in 10 μM puromycin, 2 mM 6-DMAP, as well as the histone deacetylase (HDAC) inhibitors scriptaid and nch51 for 4 to 4.5 hours. Activated constructs were cultured in HDAC inhibitor for an additional 10-16 hours, followed by culture in Global total only. Culture was performed in a MINC incubator fed with gas containing 6% $CO_2$, 5% oxygen and 89% nitrogen. Calcium-free medium was used for some of the manipulations resulting in nuclear transfer ES cells.

For some of the experiments described above additional modifications were introduced as described in Tachibana et al., 2013. Caffeine at a 1 mM concentration was added to the incubation medium during enucleation and oocyte fusion. Oocytes were activated using 2-4 pulses of 50 µs width at 2.7 kV/cm in mannitol containing fusion medium using an LF201 pulser (Nepagene), followed by 4 hours of culture in 2 mM 6-DMAP. Activated constructs were cultured in Global total containing 10% FBS and TSA for 12 hours, followed by culture to the blastocysts stage in medium containing 10% FBS.

The derivation of nuclear transfer ES cell lines from BJ fibroblasts at passage 11 was performed using nuclear transfer 30 min prior to the removal of the oocyte genome in the presence of 1 mM caffeine. Derivation of the adult cell NT-ES cell line was performed using somatic cells at passage 8, from a female subject with T1D (ID-1018, age of onset 10 y, age at study 32 y). Oocytes were transported in GMOPSplus containing 1 mM caffeine. Upon completion of the manipulation, oocytes were incubated for 45 min-1 h in calcium-free MCZB, then placed in calcium containing medium for 10 min prior to activation and culture as described above. Oocyte activation was performed within 2 hours post transfer using 4 electrical pulses, followed by incubation in medium containing HDAC inhibitors scriptaid and nch51, in addition to 10 µg/ml puromycin and 2 mM 6-DMAP for 4 hours, and thereafter, medium containing HDAC inhibitor for 15 hours. Culture was performed in a Heracell 150i incubator containing 5% CO2 at 37° C., in Global medium (IVFonline LGGG-050) containing 10% fetal bovine serum. ES cell derivation was conducted in medium containing DMEM/F12 supplemented with 10% KO-SR and 10% FBS, Rock inhibitor Y-27632, thiazovivin, non-essential amino acids, 10 ng/ml bFGF, Glutamax, and beta mercaptoethanol (all reagents from Life Technologies). Upon attachment, trophectoderm cells were ablated using laser pulses using a Lykos laser (Hamilton Thorne). Outgrowths were apparent within 10 days of plating, and were picked when colonies reached a size of about 1 mm in diameter. Passaging was done enzymatically using TrpLE (Life Technologies) and standard ES cell medium (substituting FBS with KO-SR and DMEM/F12 with KO-DMEM) using Rock inhibitor Y-27632 for the first day after plating.

Karyotyping and Cell-Line Analysis

Karyotyping of human cell lines was done by Cell Line Genetics. Gene expression analysis was performed using Illumina HumanHT-12 expression BeadChip and analyzed using the Illumina BeadStudio software. Pancreatic differentiation was performed as described[29]. Datapoints in FIG. 2 include comparisons to samples from GEO (GSE28024). Gene expression analysis of nuclear transfer ES cells and parental fibroblasts was performed using the Human Gene 1.0 ST microarray platform (Affymetrix) according to the manufacturer's protocol. Array data were analyzed using Robust Multi-array Average (RMA) in Affymetrix Expression Console. Comparisons of gene expression levels and principle component analysis included additional published samples available on GEO. Neurons were differentiated for 34 days using a modified dual SMAD inhibition protocol[30]. For beta cell differentiation, ES cells were dissociated in trypsin (Gibco), suspended in human ES medium containing 10 µM ROCK inhibitor (Y27632), plated at a density of 150,000 and 800,000 cells per well in 48 and 12-well plates respectively and beta cell differentiation was initiated 24 hours later. Detailed formulations of differentiation media were described previously[31]. Insulin secretion upon stimulation with 30 mM KCl was measured by ELISA as previously described[31]. Embryonic bodies were generated in DMEM containing 10% FBS and allowed to grow for 3-4 weeks until analysis by immunocytochemistry. For teratoma analysis, stem cells were injected subcutaneously into the dorsal flank of immunocompromised mice NOD.Cg-Prkd-$c^{scid}$ Il2rg$^{tm1Wjl}$/SzJ (Stock 005557), allowed to grow for 10-15 weeks and then subjected to histological examination with hematoxylin and eosin (HE) staining.

Cytochalasin B (Sigma) was used for removal of the nuclear genome from the oocyte. GMOPSplus (Vitrolife, #10130) was used to transport oocytes and for manipulation of oocytes. Global (IVF online #LGGG-050) was used to culture oocytes. A certified gas mixture of 5% oxygen, 6% carbon dioxide, and 89% nitrogen (Techair T202250) was used for cell culture. A vitrification kit and a cryotop thawing kit (Kitazato) were used. Humagen micropipets were used for extraction of the oocyte nuclear genome. PCR reagents used for genotyping included: primers (IDT DNA technologies) and RedTaq polymerase (Sigma). Various chemicals (from Sigma) were used: Mannitol, MgSO4, BSA, HEPES buffer (for the generation of a fusion buffer). Ionomycin and puromycin were obtained from Sigma. Inactivated Sendai virus HVJ-E was obtained from GenomeOne, Cosmo Bio. A Roche genomic DNA isolation kit was used. A gene chip Human mapping 250K Nsp Array and assay kit (Affymetrix #900767 and #900766) was used for snp genotyping of donor somatic cell DNA. The following instruments were used for all manipulations: a Nikon T2000-U microscope equipped with a Narishige micromanipulator, Oosight system, and a Tokai hit heating plate. A portable incubator (INC-RB1, CryoLogic) was used to transport oocytes. Electrofusion was performed using an LF201 electrofusion instrument (NepaGene). A Hamilton Thorne Laser system was also used. Additional details of the materials and methods used are provided elsewhere in this application and/or are well known in the art.

Whether nuclear transfer occurred before or after removal of the oocyte genome was inconsequential, and we also found no difference in efficiency of development to the blastocyst stage between adult or neonatal cells (FIG. 10D).

Calcium Imaging

The removal of the oocyte genome results in a karyoplast containing cytoplasm surrounded by a nuclear envelope. These were placed in a zona pellucida, and incubated for 30 min in fluo-4, using the fluo-4 direct calcium assay kit (Life Technologies). In brief, fluo-4 is added 1:1 to culture media. Karyoplasts were imaged both before and after exposure to inactivated Sendai virus using a Nikon TE200U microscope with an ET GFP (C92865, 96362) filter and a black and white camera and exposure time of 200 ms.

Statistical Analysis

All oocytes on which experimentation has been performed are included in this manuscript. Oocytes were randomly assigned to a specific experimental condition. There was no blinding to group allocation. To calculate whether the differences in developmental potential between different experimental conditions were significant, we compared the total number of morulae and blastocysts between different conditions. To reflect the greater developmental progression of a blastocyst versus a morula, each developmental stage was assigned a cell number: 15 for morula stage, 30 for a blastocyst. These numbers were chosen to reflect the greater number of cells contained at each developmental stage (compacted morulas contain approximately 15 cells, blastocysts at least 30 cells). Blastocysts giving rise to stem cell lines were not given greater weight in this analysis, because blastocysts giving rise to stem cell lines did not necessarily have a greater cell number (Supplementary FIG. 1). For each condition, the number of morulas was multiplied by factor 15, the number of blastocysts by factor 30. Variables were compared with Chi-square test, and the 95% confidence intervals using Graphpad Prism v. 2.01 (Graphpad Software, USA).

Example 2

The transfer of somatic cell nuclei into oocytes can give rise to stem cells and cloned animals, but often development fails at early cleavage stages with an arrest in cell proliferation. We conducted a detailed analysis of the mechanisms of developmental arrest after nuclear transfer into human and mouse oocytes and found that defects in chromosome segregation are frequent, arise prior to transcriptional activation of the genome, and required the transition through the first embryonic interphase. Chromosome segregation errors involved the formation of bridges, acentric chromosome fragments, characteristic of replication-induced errors. Their frequency was greatly increased with the state of differentiation of the donor nucleus, but reduced by the addition of histone deacetylation inhibitors. These results demonstrate that the cell type specific duplication and segregation of the genome is a defining feature of a cellular state and a limiting factor for cell cycle progression during development. Here we report methods designed to overcome this limitation.

We have previously reported that human oocytes reprogram somatic cells to a pluripotent state if the oocyte genome is not removed (Noggle et al., 2011). In the absence of the oocyte genome, nuclear transfer cells arrested cell division at the cleavage stages and failed to activate an embryonic gene expression program. In contrast, when the oocyte genome was retained, the transfer of somatic cell nuclei allowed the derivation of two stem cell lines containing a haploid oocyte genome and a reprogrammed diploid somatic cell genome. These experiments demonstrated the ability of human oocytes to reprogram a somatic cell to a pluripotent state. To develop a protocol allowing the derivation of diploid stem cell lines, we sought to better understand how the retention of the oocyte genome facilitated pre-implantation development. The triploid nature of the stem cell lines derived suggested that the extrusion of the second polar body had occurred on the genome of the oocyte, but not the genome of the somatic cell. A possible interpretation of this asymmetry is that the oocyte spindle sequesters most or all components necessary for spindle formation, and are therefore not available to transferred somatic chromatin. They would also be depleted with the removal of the oocyte genome at enucleation, which could affect the segregation of chromatin at embryonic mitosis, preventing normal development. To address these questions, we investigated spindle assembly and chromosome segregation after somatic cell nuclear transfer at both meiosis and mitosis.

Here we show that nuclear transfer embryos often arrest with karyotype abnormalities and DNA damage. Spindle assembly and chromosome segregation of somatic chromatin is normal at the second meiotic division, but chromosome segregation errors are frequent during embryonic mitoses. These errors are caused by replication of somatic chromatin in the embryonic cell, and precede the transcriptional activation of the genome. Their mechanisms of formation is not due to a failure of microtubules to attach and segregate somatic centromeres, but primarily due to a failure to normally resolve sister chromatid cohesion at anaphase of mitosis. Our results show that differences in nuclear structure and DNA replication between different cell types are functionally significant, acting as a barrier to experimentally induced cell-type transitions. We propose that the cell-type specific duplication of the genome provides a mechanism tying cell cycle progression to cell identity.

Mitotic, but not Meiotic, Segregation Errors after Human SCNT

Figures 12A, 12T:
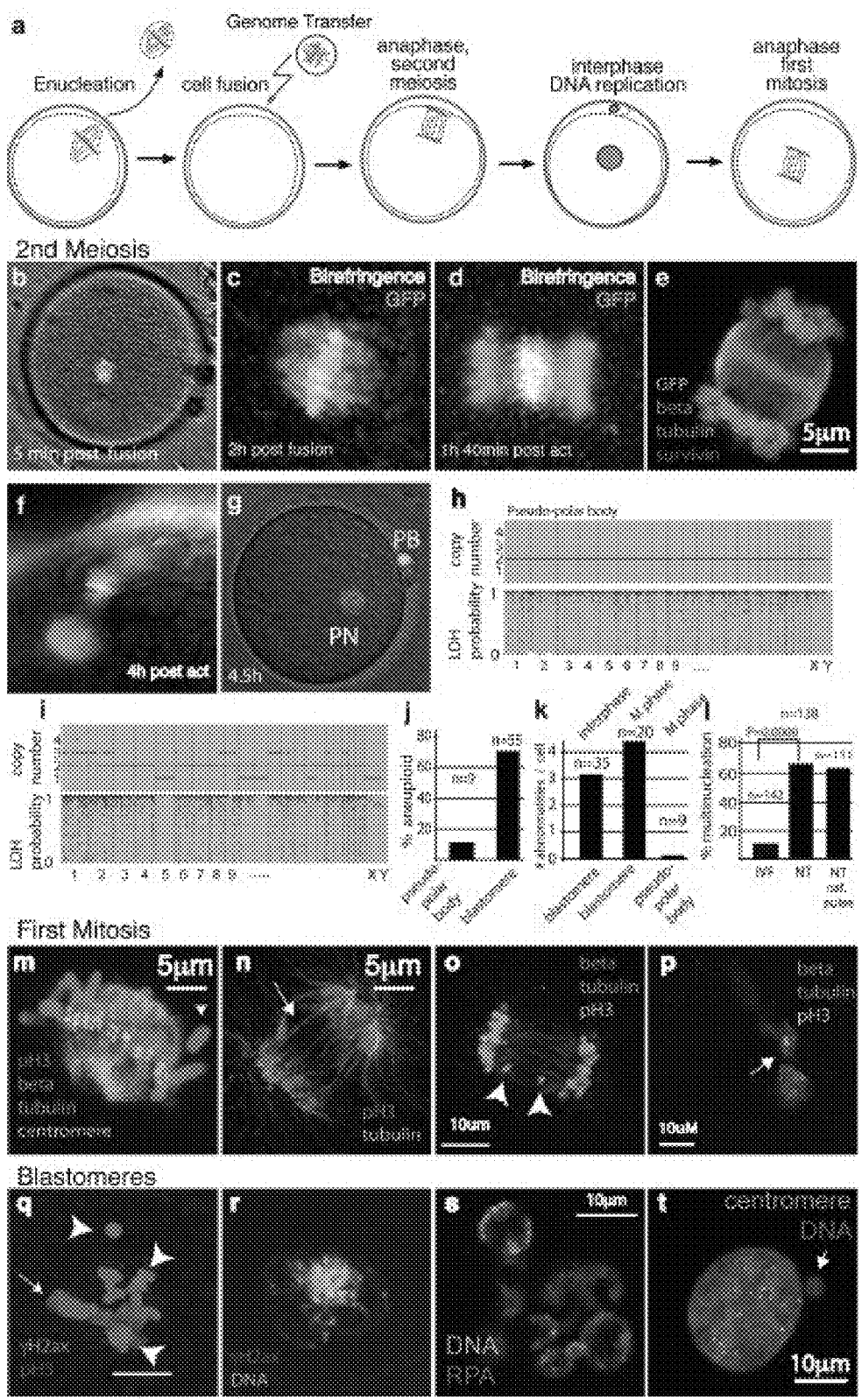
FIGS. 12A-12T. |Chromosome segregation errors in mitosis are a significant limitation to development after nuclear transfer. a, schematic of mitotic cell genome transfer. The oocyte genome is removed and replaced with a fibroblast in mitosis. The oocyte is allowed to assemble a spindle, is activated to complete the second meiotic division, thereby entering the first interphase. Cell division is analyzed at the first mitosis and in subsequent divisions. b, somatic cell genome immediately after transfer, and after 2 h (c, d, e) anaphase of somatic chromatin. f, segregation of somatic chromatin into a pseudo-polar body. g, at early interphase with a single nucleus and polar body. h, array analysis of copy number and heterozygosity. i, array analysis of copy number and heterozygosity in nuclear transfer blastomere. Representative sample. j, percentage of karyotypically abnormal pseudo-polar bodies and blastomeres. k, Average number of abnormalities per blastomere in NT embryos. Top label indicates the cell cycle of the transferred genome. l, quantification of multinucleation in nuclear transfer blastomeres and in IVF embryos. m, somatic cell genome at first mitotic metaphase. Arrowhead points to unattached chromosome lacking centromere. n, Bridge formation at first anaphase. o, chromosome fragments at first anaphase. p, chromosome string spanning midbody. Arrow indicates high pH3 staining on chromatin at midbody. q, phosphorylated γH2ax foci (arrowheads) indicating DNA damage at mitosis. Arrow points to the metaphase plate. r, phosphorylated γH2ax foci at interphase. s, Multinucleation and replication protein A (RPA) foci in interphase blastomere. t Centromere negative micronucleus in an interphase blastomere.

We next sought to determine the timing and molecular mechanism of these chromosomal abnormalities. We reasoned that if the removal of the oocyte spindle removed essential components, then these defects should be apparent at the second meiotic division. We removed the oocyte spindle-chromosome complex, and transferred the mitotic genome of a somatic cell that had been collected upon treatment with nocodazole and were kept on ice prior to transfer (FIG. 12A). Remarkably, within 1-2 hours post transfer, birefringent spindles were assembled in oocytes and chromosomes were aligned on the metaphase plate (FIGS. 12A, 12B, 12C). Upon artificial activation using a calcium ionophore and puromycin, $^{16}/_{19}$ oocytes segregated somatic cell chromatin into a polar body and formed a single pronucleus in the activated oocyte (FIG. 12F-I). And like upon segregation of oocyte chromatin, a midbody formed and the chromosome passenger complex component survivin localized to the midbody (FIG. 12E). To examine the accuracy of chromosome segregation, (pseudo-) polar bodies were biopsied and the karyotype determined using nucleotide polymorphism arrays. The karyotype was balanced, and heterozygosity present on all chromosomes, indicating that a diploid genome of 46 sister chromatids was segregated into the polar body. Of 9 polar bodies analyzed, one contained a single karyotyic abnormality, an error rate comparable to that seen upon transfer of an oocyte genome (Paull et al., 2013). Therefore, the oocyte has the ability to nucleate a spindle and accurately segregate somatic chromatin even after removal of the oocyte's own metaphaseII spindle. However, when we analyzed the karyotype of blastomeres using nucleotide arrays, we found a large number of karyotypic abnormalities (FIG. 12I-L). Of a total of 55 blastomeres, 39 (71%) were abnormal (FIG. 12I, 12J). On average, blastomeres contained 3-4 abnormalities, and they occurred both after transfer of interphase or mitotic nuclei into enucleated oocytes (FIG. 12K). In addition to numerical abnormalities, 87 of 138 blastomeres (63%) contained more than a single nucleus, significantly more often than in IVF embryos (FIG. 12L). And of 30 nuclear transfer embryos, all but one contained at least one multinucleated blastomere.

To directly observe the formation of chromosome abnormalities we analyzed spindle assembly and chromosome segregation at the first mitosis and in blastomeres. Though chromosomes could align on a metaphase plate in 3 of 4 embryos, two contained a chromosome that was not integrated into a spindle (FIG. 12M). The lack of a centromere (FIG. 12M) suggested that not a defect in the spindle apparatus, but a structural deficiency of the chromosome was responsible for a lack of spindle attachment. Upon entry into anaphase, we found anaphase bridges, chromosome fragments, lagging chromosomes and the dissociation of segregating chromosomes into several groups (FIG. 12N-P). Of 10 dividing cells, all of them contained at least one of these abnormalities. Therefore, the formation of chromosomal abnormalities could occur within the first cell cycle after somatic cell nuclear transfer. Abnormal chromosome segregation was also observed in mitotic blastomeres, with some chromosomes failing to integrate into the metaphase plate (FIG. 12Q). Such mitotic figures contained foci of phosphorylated γH2ax staining, evidence of DNA damage.

Evidence of DNA damage was also seen in blastomeres at interphase, including foci of phosphorylated γH2ax and replication protein A (RPA32) (FIG. 4R, 4S). These cells arrested at interphase, with phosphorylation of Ser10 of histone H3, indicating that these cells progressed through most of S-phase, but failed to enter mitosis. These results are consistent with our previous observation that nuclear transfer embryos upregulate transcription of Gadd45 family members (Noggle et al., 2011), proteins induced following DNA damage and capable of inducing cell cycle arrest at G2 (Wang et al., 1999). The presence of multiple nuclei in many of these blastomeres (FIG. 12S) indicated an abnormal prior mitosis. These results demonstrate that chromosome segregation errors are not due to abnormalities in the embryonic spindle apparatus, nor due to the removal of the oocyte spindle-chromosome complex, but arise during the first interphase upon transfer by an unknown mechanism.

Genomic Instability is Cell-Type and DNA Replication Dependent

To further investigate the mechanism of genomic instability after somatic cell nuclear transfer, we transferred genomes of somatic and embryonic mouse cells into enucleated mouse oocytes. As a control for our manipulations, we transplanted oocyte genomes from one MII oocyte to another. We first quantified the number of abnormal anaphase figures in unmanipulated oocytes, including bridges, fragments, and missegregating chromosomes. Abnormalities in parthenotes were few, or less than 5 percent at anaphase of the second meiosis and the first mitosis (FIG. 13A). The transfer of the oocyte genome (ONGT=oocyte nuclear genome transfer) from one oocyte to another did not increase the frequency of these abnormalities, neither at the second meiosis, nor at the first mitosis. Cultured cells showed slightly higher formation of chromosome bridges and missegregating chromosomes than oocytes, or 6.3% for fibroblasts, and 8.2% for ES cells. Upon transfer of mitotic fibroblast or ES cell genomes into MII oocytes, the frequency of these abnormalities remained unaltered, or 6% and 6.9%. However, at the first mitosis, both ES cells and fibroblasts showed a significant increase in abnormally segregating chromosomes (FIG. 13A, 13C). Abnormal anaphase figures were further increased when using interphase genomes of either cumulus cells or T cells. These results demonstrate that the frequency of abnormal chromosome segregation at mitosis is greatly dependent on the developmental stage of the transferred genome (FIG. 13A).

As different cell types are known to differ in their gene expression pattern, we first determined whether gene expression during the first cell cycle was required for a normal chromosome segregation at the first embryonic mitosis. The addition of the polymerasell inhibitor alpha amanitin to the culture medium did not significantly increase the frequency of normal mitotic figures (FIG. 13A). As cell-type specific gene expression appeared to be irrelevant to chromosome segregation at the first mitosis, we investigated whether other cell-type specific properties of the genome were of importance. It appeared conceivable that for normal chromosome segregation, the prior duplication of the genome at interphase must also be normal. To distinguish whether the chromosome segregation we observed were due to abnormal spindle attachment to chromosomes or due to structural deficiencies that can arise during DNA replication, we stained anaphases with antibodies recognizing centromeres. All chromosomes (31/31) that failed to segregate to the spindle poles lacked a centromere (FIG. 13D, 13E). Chromosome bridges contained a centromere mark that moved towards the spindle pole, but centromeres lagged behind normally segregating chromosomes (8/8) (FIG. 13D). Lagging chromosomes were found to occur in pairs, protruding from each side of a group of anaphase chromosomes (FIG. 13F, 13G mouse). These chromosomes too contained a delayed centromere, and probably formed bridges at an earlier time point of anaphase. Though we cannot exclude that some bridges are successfully resolved without damage to the genome, we found chromatin in the midbody of 2-cell embryos at interphase (FIG. 13H), and evidence for DNA damage in interphase blastomeres (FIG. 13I). Nuclear transfer embryos were most frequently affected by chromosomes that did not incorporate into the spindle, followed by bridges and lagging chromosomes (FIG. 13K). These defects are reminiscent of those caused by DNA replication stress in somatic cells (Chan et al., 2009).

To determine whether other parameters known to affect the developmental efficiency after somatic cell nuclear transfer affected the fidelity of segregation at the first mitosis, we investigated the role of the nuclear structure. To preserve a somatic nuclear structure, we enucleated oocytes as before, but transferred somatic cell nuclei only after activation and inhibition of meiotic kinases using 6-dmap. During artificial activation, kinase levels decrease, compromising the ability to break down the nuclear envelope and induce chromosome condensation. When nuclei are transferred at prometaphase of mitosis, somatic chromatin condenses, allowing an efficient transition to a nucleus of embryonic morphology, while nuclei transferred after activation retain a somatic morphology (Egli et al., 2011). We transferred somatic nuclei within the first hour post activation, and analyzed chromosome segregation at the first mitosis. The large majority (90%) of dividing embryos were severely abnormal (FIG. 13L), most containing a string of chromatin between the segregating spindle poles (FIG. 13M). Therefore, the reduction in kinase activities was detrimental to the ability of oocytes to prepare somatic chromatin for progression through the first cell cycle.

Most importantly, the addition of the histone deacetylation inhibitor scriptaid decreased the frequency of chromosome segregation errors (FIG. 13L). Other epigenetic modifiers, including different histone deacetylase inhibitors, as well as histone methylation inhibitors may have similar beneficial effects.

Discussion

Here we describe frequent chromosome segregation errors after somatic cell nuclear transfer into human oocytes. These defects are not due to the depletion of spindle components removed with the oocyte chromatin, and they are not due to the transfer procedure itself. In addition, they occur prior to the major wave of embryonic genome activation in human (Braude et al., 1988) and are not caused by a lack of embryonic transcription. Using different donor cell types in mouse embryos, we found a tight correlation of segregation errors with the state of differentiation of the donor cell, which in turn correlates with developmental potential. The nature of chromosome segregation errors, including bridges and acentric chromosomes, are reminiscent to those observed after DNA replication stress (Burrell et al., 2013; Chan et al., 2009), and their frequency is altered by the presence of additional nucleosides, compounds known to affect the activity of origins. Therefore, our results demonstrate that cell-type specific differences in DNA replication are a functionally important barrier to cell reprogramming, and perhaps more generally, to cell type transitions.

Differences in gene expression are a defining feature of different cell types. A large body of literature contributed to a better understanding of gene expression changes in development, differentiation and reprogramming. On the basis of this work, the mechanisms of cell reprogramming and development are often interpreted exclusively in the context of changes in gene expression (Hanna et al., 2010; Jaenisch and Young, 2008). For instance, incomplete reactivation of embryonic genes is thought to be a major cause for the developmental failure of mouse clones (Boiani et al., 2002; Bortvin et al., 2003; Humpherys et al., 2002). Such emphasis on gene expression in cell-type reprogramming implies that progression through S-phase can occur independently of the regulators that determine cell identity. This model is at first sight attractive, because it confers the ability to progress through S-phase to the many cell types arising during development and cell differentiation, but also to abnormal cells, including tumor cells. However, the data presented here, and those by others, question this model. Nuclear transfer embryos with incomplete reprogramming arrest during early development (Noggle et al., 2011), and only reprogrammed cells continue proliferation to yield ES cells equivalent to those of fertilized embryos (Brambrink et al., 2006). Therefore, the ability of cells to progress through S-phase and as a consequence through a normal M-phase depends on cell-type specific factors, tying cell proliferation to a specific cell identity.

DNA replication progresses in cell-type specific temporal patterns, and differs in even closely related cell types (Hiratani et al., 2010; Ryba et al., 2011). Upon reprogramming to induced pluripotent stem cells, or after somatic cell nuclear transfer, DNA replication timing is changed from a somatic to an embryonic pattern (Hiratani et al., 2010; Shufaro et al., 2010). While Hiratani and colleagues used a genome-wide approach and discovered regions of replication timing that are difficult to reprogram, Shufaro and colleagues examined a small number of developmental genes that were efficiently reprogrammed. The recent finding that oocytes remodel chromatin in a context-dependent manner, with efficient removal of DNA methylation at gene promoters, but inefficiently at LINE and LTR repeats (Chan et al., 2012), suggests that the reprogramming of DNA replication timing may also sometimes be incomplete.

Some of the factors regulating cell-type specific DNA replication may be identical to those regulating cell-type specific gene expression. Both processes depend on the three-dimensional organization of the nucleus. When a somatic cell nuclear structure is preserved in embryonic cells, normal progression through the cell cycle cannot occur. Similarly, when nuclear transfer is performed in mouse zygotes without remodeling of the somatic nuclear structure, embryonic gene expression fails (Egli et al., 2011). As most proliferating cells undergo gene expression as well as DNA replication, it is challenging to distinguish effects of the experimental manipulation on gene expression from effects on DNA replication. For instance histone deacetylase inhibitors used to increase reprogramming efficiency to iPS cells (Huangfu et al., 2008) are known to alter the activity of replication origins (Kemp et al., 2005) and gene expression. And c-myc, a protein used with Oct-4, Sox-2 and Klf4 to generate iPS cells stimulates both transcription (Kato et al., 1990) and DNA replication (Dominguez-Sola et al., 2007). Nuclear transfer into oocytes provides a suitable model excluding gene expression as a relevant factor, because the proteins and mRNA required for normal cell cycle progression are provided maternally within the egg. We hypothesize that the cell type specificity of DNA replication provides a mechanism to control and limit cell proliferation depending on cell state, in processes as diverse as aging, tumor formation, reprogramming, development and differentiation.

Immunocytochemistry

Oocytes and nuclear transfer cells were analyzed using the following antibodies recognizing beta tubulin (Millipore 05-661), anti-centromere (15-235-0001 Antibodies Inc), phospho-histone H3 Ser10 (Millipore 06-570), borealin (MBL Int Corp 147-3). Images were taken using a Zeiss LSM710 confocal microscope, or a Zeiss LSMS Pascal microscope. Immunostaining of human stem cell lines was done using antibodies for OCT4 (09-0023, Stemgent), nanog (Cell Signaling Technologies D73G4), Tra1-81 (MAB4381 Millipore), and SSEA-4, anti-TRA1-60 (MAB4360; Millipore), PDX1 (R&D AF2419), Insulin (Millipore 05-1109), rabbit anti-AFP (A000829; DAKO) and rabbit anti-TUJ1 (T3952; Sigma-Aldrich). Hoechst33342 (Sigma) was used for the staining of DNA, secondary antibodies are from LifeTechnologies. Cells were fixed in 2% PFA in PBS containing 2.5% Triton-X100 at RT for about 10-15 min. Cells were washed, blocked with FBS and incubated with primary antibodies. Images were taken using an Olympus IX71 epifluorescence microscope and an Olympus DP30 monochrome camera. Figures for publication were assembled in Adobe Illustrator.

Nuclear transfer methods in this Example are identical to those described in Example 1.

Example 3

Use of Metaphase Somatic Cells for Nuclear Transfer

Experiments were performed in which the nuclear genome was removed from an oocyte at the metaphase II stage to form an enucleated oocyte. A somatic cell at mitosis was then transferred into/fused with the oocyte using inactivated Sendai virus. The reconstructed oocyte was then cultured in the incubator (6% CO2, 5% O2, 89% N2, at 37° C.), for 2 hours. The reconstructed oocyte comprising the somatic cell genome was then placed in an incubator and activated using a calcium ionophore at a concentration of 2.5 µM in calcium free medium to induce a calcium pulse of a physiological amplitude. Upon activation, the egg was placed in medium containing 10 µg/ml puromycin (a translation inhibitor). The medium also contained 10 ng/ml of scriptaid—a histone deacetylation inhibitor. After 3.4-4 hours, the medium was changed to a medium containing only 41 ng/ml scriptaid (but not puromycin) and maintained for 15 to 17 hours post activation. The scriptaid medium was then removed and embryos were cultured in Globaltotal medium. FIG. 4A provides a schematic diagram of the protocol proceeding from enucleation of the oocyte, to fusion of the enucleated oocyte with a somatic cell in mitosis, and then spindle assembly of the transferred somatic cell genome. FIG. 12B-12E show spindle assembly after nuclear transfer of a somatic cell genome. While some have claimed success using human cells also (see French et al. 2008), others have found that the development of human oocytes after genome exchange arrests at late cleavage stages if the oocyte genome is removed (see Noggle et al. 2011). The novel techniques described and exemplified herein allow efficient reprogramming and development to the blastocyst stage. Developmental competence of nuclear transfer embryos to the blastocyst stage, as achieved here, is necessary for the derivation of pluripotent stem cell lines.

Methods

Methods are identical to Example 1, with the exception of omitting 6-dmap during oocyte activation. The somatic cell may be fused in calcium-free medium or incubated in BAPTA-AM prior to transfer to ensure maintenance of the mitotic state.

REFERENCE LIST

Each of the references listed below, and all other references cited in this patent application, are hereby incorporated by reference in their entireties.

REFERENCES LISTED BY FIRST AUTHOR

Byrne, J. A., Pedersen, D. A., Clepper, L. L., Nelson, M., Sanger, W. G., Gokhale, S., Wolf, D. P., and Mitalipov, S. M. 2007. Producing primate embryonic stem cells by somatic cell nuclear transfer. Nature 450(7169): 497-502.

Chung, Y., Bishop, C. E., Treff, N. R., Walker, S. J., Sandler, V. M., Becker, S., Klimanskaya, I., Wun, W. S., Dunn, R., Hall, R. M. et al. 2009. Reprogramming of human somatic cells using human and animal oocytes. Cloning Stem Cells 11(2): 213-223.

French et al., 2008. Development of human cloned blastocysts following somatic cell nuclear transfer with adult fibroblasts. Stem Cells 26(2):485-93.

Wakayama, T., Tabar, V., Rodriguez, I., Perry, A. C., Studer, L., and Mombaerts, P. 2001. Differentiation of embryonic stem cell lines generated from adult somatic cells by nuclear transfer. Science 292(5517): 740-743.

Wilmut, I., Schnieke, A. E., McWhir, J., Kind, A. J., and Campbell, K. H. 1997. Viable offspring derived from fetal and adult mammalian cells. Nature 385(6619): 810-813.

U.S. Patent Application Pub. No. US2012/0129620, by Egli et al.

Boiani, M., Eckardt, S., Scholer, H. R. and McLaughlin, K. J. (2002). Oct4 distribution and level in mouse clones: consequences for pluripotency. Genes Dev 16, 1209-19.

Bortvin, A., Eggan, K., Skaletsky, H., Akutsu, H., Berry, D. L., Yanagimachi, R., Page, D. C. and Jaenisch, R. (2003). Incomplete reactivation of Oct4-related genes in mouse embryos cloned from somatic nuclei. Development 130, 1673-80.

Brambrink, T., Hochedlinger, K., Bell, G. and Jaenisch, R. (2006). ES cells derived from cloned and fertilized blastocysts are transcriptionally and functionally indistinguishable. Proc Natl Acad Sci USA 103, 933-8.

Braude, P., Bolton, V. and Moore, S. (1988). Human gene expression first occurs between the four- and eight-cell stages of preimplantation development. Nature 332, 459-61.

Bui, H. T., Wakayama, S., Kishigami, S., Park, K. K., Kim, J. H., Thuan, N. V. and Wakayama, T. (2010). Effect of trichostatin A on chromatin remodeling, histone modifications, DNA replication, and transcriptional activity in cloned mouse embryos. Biol Reprod 83, 454-63.

Burrell, R. A., McClelland, S. E., Endesfelder, D., Groth, P., Weller, M. C., Shaikh, N., Domingo, E., Kanu, N., Dewhurst, S. M., Gronroos, E. et al. (2013). Replication stress links structural and numerical cancer chromosomal instability. Nature 494, 492-6.

Chan, K. L., Palmai-Pallag, T., Ying, S. and Hickson, I. D. (2009). Replication stress induces sister-chromatid bridging at fragile site loci in mitosis. Nat Cell Biol 11, 753-60.

Chan, M. M., Smith, Z. D., Egli, D., Regev, A. and Meissner, A. (2012). Mouse ooplasm confers context-specific reprogramming capacity. Nat Genet 44, 978-80.

Dominguez-Sola, D., Ying, C. Y., Grandori, C., Ruggiero, L., Chen, B., Li, M., Galloway, D. A., Gu, W., Gautier, J. and Dalla-Favera, R. (2007). Non-transcriptional control of DNA replication by c-Myc. Nature 448, 445-51.

Egli, D., Chen, A. E., Saphier, G., Ichida, J., Fitzgerald, C., Go, K. J., Acevedo, N., Patel, J., Baetscher, M., Kearns, W. G. et al. (2011). Reprogramming within hours following nuclear transfer into mouse but not human zygotes. Nat Commun 2, 488.

Hanna, J. H., Saha, K. and Jaenisch, R. (2010). Pluripotency and cellular reprogramming: facts, hypotheses, unresolved issues. Cell 143, 508-25.

Hiratani, I., Ryba, T., Itoh, M., Rathjen, J., Kulik, M., Papp, B., Fussner, E., Bazett-Jones, D. P., Plath, K., Dalton, S. et al. (2010). Genome-wide dynamics of replication timing revealed by in vitro models of mouse embryogenesis. Genome Res 20, 155-69.

Huangfu, D., Maehr, R., Guo, W., Eijkelenboom, A., Snitow, M., Chen, A. E. and Melton, D. A. (2008). Induction of pluripotent stem cells by defined factors is greatly improved by small-molecule compounds. Nat Biotechnol 26, 795-7.

Humpherys, D., Eggan, K., Akutsu, H., Friedman, A., Hochedlinger, K., Yanagimachi, R., Lander, E. S., Golub, T. R. and Jaenisch, R. (2002). Abnormal gene expression in cloned mice derived from embryonic stem cell and cumulus cell nuclei. Proc Natl Acad Sci USA 99, 12889-94.

Jaenisch, R. and Young, R. (2008). Stem cells, the molecular circuitry of pluripotency and nuclear reprogramming. Cell 132, 567-82.

Kato, G. J., Barrett, J., Villa-Garcia, M. and Dang, C. V. (1990). An amino-terminal c-myc domain required for neoplastic transformation activates transcription. Mol Cell Biol 10, 5914-20.

Kemp, M. G., Ghosh, M., Liu, G. and Leffak, M. (2005). The histone deacetylase inhibitor trichostatin A alters the pattern of DNA replication origin activity in human cells. Nucleic Acids Res 33, 325-36.

Kishigami, S., Mizutani, E., Ohta, H., Hikichi, T., Thuan, N. V., Wakayama, S., Bui, H. T. and Wakayama, T. (2006). Significant improvement of mouse cloning technique by treatment with trichostatin A after somatic nuclear transfer. Biochem Biophys Res Commun 340, 183-9.

Noggle, S., Fung, H. L., Gore, A., Martinez, H., Satriani, K. C., Prosser, R., Oum, K., Paull, D., Druckenmiller, S., Freeby, M. et al. (2011). Human oocytes reprogram somatic cells to a pluripotent state. Nature 478, 70-5.

Paull, D., Emmanuele, V., Weiss, K. A., Treff, N., Stewart, L., Hua, H., Zimmer, M., Kahler, D. J., Goland, R. S., Noggle, S. A. et al. (2013). Nuclear genome transfer in human oocytes eliminates mitochondrial DNA variants. Nature 493, 632-7.

Robinton, D. A. and Daley, G. Q. (2012). The promise of induced pluripotent stem cells in research and therapy. Nature 481, 295-305.

Ryba, T., Hiratani, I., Sasaki, T., Battaglia, D., Kulik, M., Zhang, J., Dalton, S. and Gilbert, D. M. (2011). Replication timing: a fingerprint for cell identity and pluripotency. PLoS Comput Biol 7, e1002225.

Rybouchkin, A., Kato, Y. and Tsunoda, Y. (2006). Role of histone acetylation in reprogramming of somatic nuclei following nuclear transfer. Biol Reprod 74, 1083-9.

Schwartz, S. D., Hubschman, J. P., Heilwell, G., Franco-Cardenas, V., Pan, C. K., Ostrick, R. M., Mickunas, E., Gay, R., Klimanskaya, I. and Lanza, R. (2012). Embryonic stem cell trials for macular degeneration: a preliminary report. Lancet 379, 713-20.

Shufaro, Y., Lacham-Kaplan, O., Tzuberi, B. Z., McLaughlin, J., Trounson, A., Cedar, H. and Reubinoff, B. E. (2010). Reprogramming of DNA replication timing. Stem Cells 28, 443-9.

Tabar, V., Tomishima, M., Panagiotakos, G., Wakayama, S., Menon, J., Chan, B., Mizutani, E., Al-Shamy, G., Ohta, H., Wakayama, T. et al. (2008). Therapeutic cloning in individual parkinsonian mice. Nat Med 14, 379-81.

Tachibana, M., Amato, P., Sparman, M., Gutierrez, N. M., Tippner-Hedges, R., Ma, H., Kang, E., Fulati, A., Lee, H.-S., Sritanaudomchai, H. et al. (2013a). Human Embryonic Stem Cells Derived by Somatic Cell Nuclear Transfer Cell.

Tachibana, M., Amato, P., Sparman, M., Gutierrez, N. M., Tippner-Hedges, R., Ma, H., Kang, E., Fulati, A., Lee, H. S., Sritanaudomchai, H. et al. (2013b). Human Embryonic Stem Cells Derived by Somatic Cell Nuclear Transfer. Cell.

Wang, X. W., Zhan, Q., Coursen, J. D., Khan, M. A., Kontny, H. U., Yu, L., Hollander, M. C., O'Connor, P. M., Fornace, A. J., Jr. and Harris, C. C. (1999). GADD45 induction of a G2/M cell cycle checkpoint. Proc Natl Acad Sci USA 96, 3706-11.

NUMERICAL LISTING OF REFERENCES

1. Gurdon, J. B., Elsdale, T. R., & Fischberg, M., Sexually mature individuals of Xenopus laevis from the transplantation of single somatic nuclei. Nature 182 (4627), 64-65 (1958).
2. Noggle, S. et al., Human oocytes reprogram somatic cells to a pluripotent state. Nature 478 (7367), 70-75 (2011).
3. Tachibana, M. et al., Human embryonic stem cells derived by somatic cell nuclear transfer. Cell 153 (6), 1228-1238 (2013).
4. Cyranoski, D., Verdict: Hwang's human stem cells were all fakes. Nature 439 (7073), 122-123 (2006).
5. Chung, Y. et al., Reprogramming of human somatic cells using human and animal oocytes. Cloning Stem Cells 11 (2), 213-223 (2009).
6. Hall, V. J. et al., Developmental competence of human in vitro aged oocytes as host cells for nuclear transfer. Hum Reprod 22 (1), 52-62 (2007).
7. Greggains, G. D. et al., Therapeutic potential of somatic cell nuclear transfer for degenerative disease caused by mitochondrial DNA mutations. Sci Rep 4, 3844 (2014).
8. Egli, D. et al., Reprogramming within hours following nuclear transfer into mouse but not human zygotes. Nat Commun 2, 488 (2011).
9. Stojkovic, M. et al., Derivation of a human blastocyst after heterologous nuclear transfer to donated oocytes. Reprod Biomed Online 11 (2), 226-231 (2005).
10. French, A. J. et al., Development of human cloned blastocysts following somatic cell nuclear transfer with adult fibroblasts. Stem Cells 26 (2), 485-493 (2008).
11. Li, J. et al., Human embryos derived by somatic cell nuclear transfer using an alternative enucleation approach. Cloning Stem Cells 11 (1), 39-50 (2009).
12. Fan, Y. et al., Derivation of cloned human blastocysts by histone deacetylase inhibitor treatment after somatic cell nuclear transfer with beta-thalassemia fibroblasts. Stem Cells Dev (2011).
13. Wakayama, T., Perry, A. C., Zuccotti, M., Johnson, K. R., & Yanagimachi, R., Full-term development of mice from enucleated oocytes injected with cumulus cell nuclei. Nature 394 (6691), 369-374 (1998).
14. Liu, L., Oldenbourg, R., Trimarchi, J. R., & Keefe, D. L., A reliable, noninvasive technique for spindle imaging and enucleation of mammalian oocytes. Nat Biotechnol 18 (2), 223-225 (2000).
15. Gassmann, R. et al., Borealin: a novel chromosomal passenger required for stability of the bipolar mitotic spindle. J Cell Biol 166 (2), 179-191 (2004).
16. Kishigami, S. et al., Significant improvement of mouse cloning technique by treatment with trichostatin A after somatic nuclear transfer. Biochem Biophys Res Commun 340 (1), 183-189 (2006).
17. Rybouchkin, A., Kato, Y., & Tsunoda, Y., Role of histone acetylation in reprogramming of somatic nuclei following nuclear transfer. Biol Reprod 74 (6), 1083-1089 (2006).
18. Paull, D. et al., Nuclear genome transfer in human oocytes eliminates mitochondrial DNA variants. Nature 493 (7434), 632-637 (2013).
19. Braude, P., Bolton, V., & Moore, S., Human gene expression first occurs between the four- and eight-cell stages of preimplantation development. Nature 332 (6163), 459-461 (1988).
20. Kind, A. & Colman, A., Therapeutic cloning: needs and prospects. Semin Cell Dev Biol 10 (3), 279-286 (1999).
21. Rideout, W. M., 3rd, Hochedlinger, K., Kyba, M., Daley, G. Q., & Jaenisch, R., Correction of a genetic defect by nuclear transplantation and combined cell and gene therapy. Cell 109 (1), 17-27 (2002).
22. Tabar, V. et al., Therapeutic cloning in individual parkinsonian mice. Nat Med 14 (4), 379-381 (2008).
23. Klitzman, R. & Sauer, M. V., Payment of egg donors in stem cell research in the USA. Reprod Biomed Online 18 (5), 603-608 (2009).
24. Egli, D. et al., Impracticality of egg donor recruitment in the absence of compensation. Cell Stem Cell 9 (4), 293-294 (2011).
25. Choudhary, M. et al., Egg sharing for research: a successful outcome for patients and researchers. Cell Stem Cell 10 (3), 239-240 (2012).
26. Medicine, E.C.O.T.A.S.F.R., Financial compensation of oocyte donors. Fertil Steril 88 (2), 305-309 (2007).
27. Daley, G. Q. et al., Ethics. The ISSCR guidelines for human embryonic stem cell research. Science 315 (5812), 603-604 (2007).
28. Tachibana, M., Sparman, M., & Mitalipov, S., Chromosome transfer in mature oocytes. Nat Protoc 5 (6), 1138-1147 (2010).
29. Hua, H. et al., iPSC-derived beta cells model diabetes due to glucokinase deficiency. J Clin Invest (2013).
30. Chambers, S. M. et al., Highly efficient neural conversion of human ES and iPS cells by dual inhibition of SMAD signaling. Nat Biotechnol 27 (3), 275-280 (2009).
31. Shang, L. et al., Beta cell dysfunction due to increased ER stress in a stem cell model of Wolfram syndrome. Diabetes (2013).

What is claimed is:

1. A method for producing a diploid human nuclear transfer embryo capable of developing into a blastocyst containing an inner cell mass, the method comprising:
   a) obtaining a diploid nuclear genome from a postnatal human somatic cell,
   b) obtaining an enucleated mature human oocyte,
   c) transferring the diploid nuclear genome into the enucleated mature human oocyte to form a reconstructed oocyte, wherein the transferring is performed in a medium that is calcium-free,
   d) subsequently contacting the reconstructed oocyte with a calcium ionophore, an inhibitor of translation, and optionally an inhibitor of meiotic kinases, to activate the reconstructed oocyte and promote entry into interphase, and e) contacting the reconstructed oocyte with a histone deacetylase inhibitor and/or a histone methylation inhibitor, thereby producing a diploid human nuclear transfer embryo capable of developing into a blastocyst containing an inner cell mass.

2. The method of claim 1, wherein the inhibitor of translation is puromycin and the inhibitor of meiotic kinases is 6-DMAP.

3. The method of claim 2, wherein the puromycin is used at approximately 10 μM and wherein the 6-DMAP is used at approximately 2 mM.

4. The method of claim 1, wherein step (c) comprises using a fusogenic agent.

5. The method of claim 4, wherein the fusogenic agent is used at the minimum concentration sufficient to induce cell fusion.

6. The method of claim 4, wherein the fusogenic agent is an inactivated Sendai virus Sendai virus HVJ-E.

7. The method of claim 1, wherein the histone deacetylase inhibitor is selected from the group consisting of Scriptaid, Nch51 and trichostatin.

8. The method of claim 1, wherein the reconstructed oocyte, or embryo derived from the reconstructed oocyte, is contacted with the histone deacetylase inhibitor(s) for approximately 14 to approximately 21 hours post activation, or until just prior to the first mitosis.

* * * * *